(12) United States Patent
Bode et al.

(10) Patent No.: US 12,190,749 B2
(45) Date of Patent: Jan. 7, 2025

(54) APPARATUSES FOR SIMULATING DENTAL PROCEDURES AND METHODS

(71) Applicant: SIMtoLIFE B.V., Amsterdam (NL)

(72) Inventors: Dyon Bode, Copenhagen (DK); Dennis Brinkman, Copenhagen (DK); Niels Van Den Braber, Copenhagen (DK); Karel Van Gelder, Copenhagen (DK)

(73) Assignee: SIMtoLIFE B.V., Amsterdam (NL)

( * ) Notice: Subject to any disclaimer, the term of this patent is extended or adjusted under 35 U.S.C. 154(b) by 123 days.

(21) Appl. No.: 17/633,703

(22) PCT Filed: Aug. 4, 2020

(86) PCT No.: PCT/EP2020/071871
§ 371 (c)(1),
(2) Date: Feb. 8, 2022

(87) PCT Pub. No.: WO2021/028260
PCT Pub. Date: Feb. 18, 2021

(65) Prior Publication Data
US 2022/0319355 A1    Oct. 6, 2022

(30) Foreign Application Priority Data

Aug. 9, 2019  (DK) .............................. PA201970503
Aug. 9, 2019  (DK) .............................. PA201970504
(Continued)

(51) Int. Cl.
*G09B 23/28*    (2006.01)
*A61B 34/10*    (2016.01)
(Continued)

(52) U.S. Cl.
CPC ............ *G09B 23/283* (2013.01); *A61B 34/10* (2016.02); *G06F 3/011* (2013.01); *G06F 3/0346* (2013.01);
(Continued)

(58) Field of Classification Search
CPC ...... G09B 23/283; G09B 23/00; A61B 34/10; A61B 2034/102; A61B 2034/105;
(Continued)

(56) References Cited

U.S. PATENT DOCUMENTS

| 8,716,973 B1 * | 5/2014 | Lammertse | ............ A61B 34/77 345/184 |
| 2006/0019228 A1 * | 1/2006 | Riener | ................. G09B 23/283 434/263 |

(Continued)

FOREIGN PATENT DOCUMENTS

| CN | 107205795 A | 9/2017 |
| JP | H1165426 A | 3/1999 |

(Continued)

OTHER PUBLICATIONS

Tse et al, "Design and Development of a Haptic Dental Training System—hapTEL", Analytics in the Social and Ubiquitous Context: 5th International Workshop on Modeling Social Media, XP047400420, ISBN: 978-3-642-17318-9, Jul. 8, 2010, 8 pages.

(Continued)

*Primary Examiner* — Jack Yip
(74) *Attorney, Agent, or Firm* — Nordic Patent Service

(57) ABSTRACT

A dental procedure simulator includes a support structure and a linkage suspended from the support structure. The linkage is controlled by a computer that is configured to simulate a dental procedure or treatment. A handpiece is coupled to the linkage and configured to be held in a hand of a user and to be manipulated by the user in a workspace (Continued)

(W) in real space. The phenom head is provided with a phantom upper jaw and a phantom lower jaw (14) and is supported by the support structure and arranged in the workspace (W.) The phantom lower jaw is arranged movably relative to the phantom upper jaw.

20 Claims, 12 Drawing Sheets

(30) Foreign Application Priority Data

| Aug. 9, 2019 | (DK) | ............................ PA201970505 |
|---|---|---|
| Aug. 9, 2019 | (DK) | ............................ PA201970506 |
| Aug. 9, 2019 | (DK) | ............................ PA201970507 |
| Aug. 9, 2019 | (DK) | ............................ PA201970508 |

(51) Int. Cl.
G06F 3/01 (2006.01)
G06F 3/0346 (2013.01)

(52) U.S. Cl.
CPC ... *A61B 2034/102* (2016.02); *A61B 2034/105* (2016.02)

(58) Field of Classification Search
CPC . A61B 2034/104; G06F 3/011; G06F 3/0346; A61C 1/00; A61C 19/00
See application file for complete search history.

(56) References Cited

U.S. PATENT DOCUMENTS

| 2008/0176198 | A1* | 7/2008 | Ansari | ................. G09B 23/283 |
| | | | | 434/270 |
| 2011/0245951 | A1* | 10/2011 | Gantes | ..................... A61B 6/51 |
| | | | | 700/98 |
| 2012/0026307 | A1* | 2/2012 | Price | ................... G09B 23/283 |
| | | | | 348/66 |
| 2014/0106326 | A1* | 4/2014 | Hemmer | .............. G09B 23/283 |
| | | | | 434/264 |
| 2014/0342324 | A1* | 11/2014 | Ghovanloo | .............. G09B 5/06 |
| | | | | 434/185 |
| 2018/0110603 | A1* | 4/2018 | Stipek, Sr. | ............. A61C 11/06 |
| 2018/0293802 | A1* | 10/2018 | Hendricks | .............. G09B 23/30 |
| 2019/0019434 | A1* | 1/2019 | Hastings | ................ G09B 23/32 |
| 2019/0096285 | A1 | 3/2019 | Bode | |
| 2019/0325785 | A1* | 10/2019 | Huang | .................... G06F 3/011 |
| 2019/0350685 | A1* | 11/2019 | Saghatchi | ............ A61C 8/0089 |
| 2020/0005676 | A1* | 1/2020 | Kubota | .................... G09B 9/00 |
| 2021/0192759 | A1* | 6/2021 | Lang | ......................... G06T 3/40 |
| 2021/0312834 | A1* | 10/2021 | Maddahi | .............. G09B 23/283 |

FOREIGN PATENT DOCUMENTS

| JP | 2010231167 | A | 10/2010 |
| JP | 2011527462 | A | 10/2011 |
| JP | 2019512299 | A | 5/2019 |
| WO | 2010071533 | A1 | 6/2010 |
| WO | 2012002487 | A1 | 1/2012 |
| WO | 2014050543 | A1 | 4/2014 |
| WO | 2017153416 | A1 | 9/2017 |
| WO | 2018168842 | A1 | 9/2018 |

OTHER PUBLICATIONS

Wang et al, "Survey on multisensory feedback virtual reality dental training systems", European Journal of Dental Education, vol. 20, No. 4, pp. 248-260, XP055377378, ISSN: 1396-5883, DOI: 10.1111/eje.12173, Nov. 7, 2015, 13 pages.
International Search Report, Application No. PCT/EP2020/071871, Mailed Jan. 27, 2021, 6 pages.
Japan Patent Office, Notification of reasons for refusal, Application No. 2022-507796, dated Apr. 24, 2024, 9 pages, English Translation, 11 pages.
Japan Patent Office, Notice of Reasons for Refusal, Application No. 2022-507796, mailed Aug. 29, 2024, 4 pages. English Translation, 4 pages.
The State Intellectual Property Office of People's Republic of China, The First Office Action, Application No. 202080056277.X, mailed Jul. 24, 2024, 14 pages, English Translation, 7 pages.

\* cited by examiner

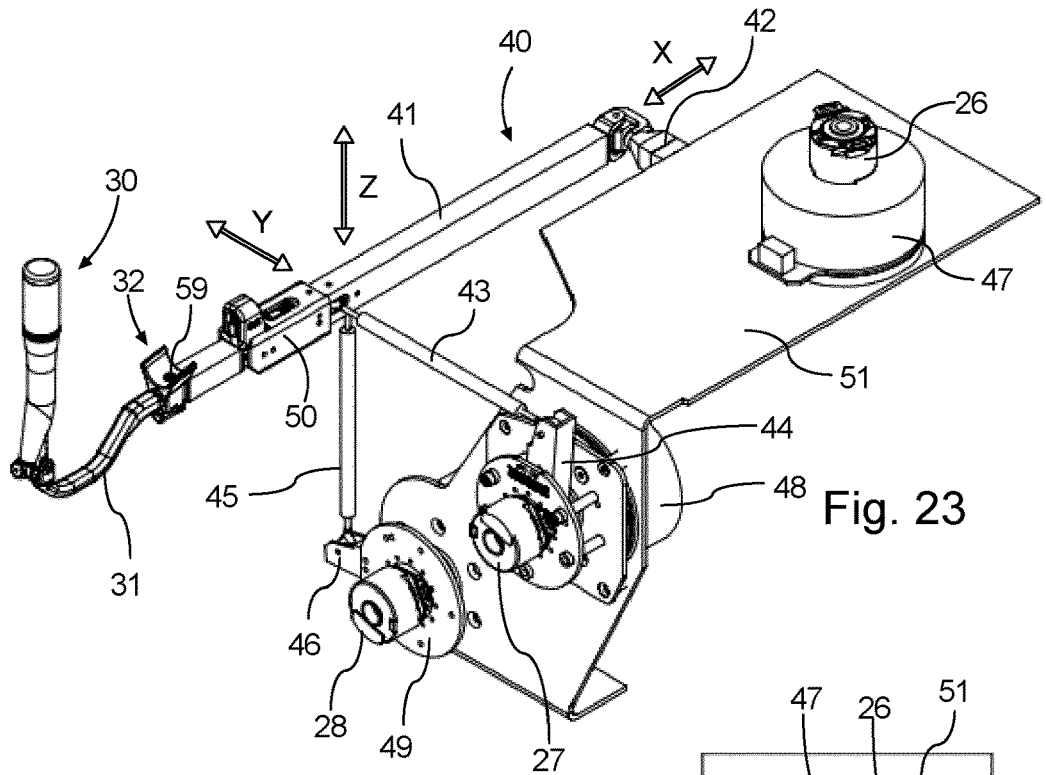
Fig. 23
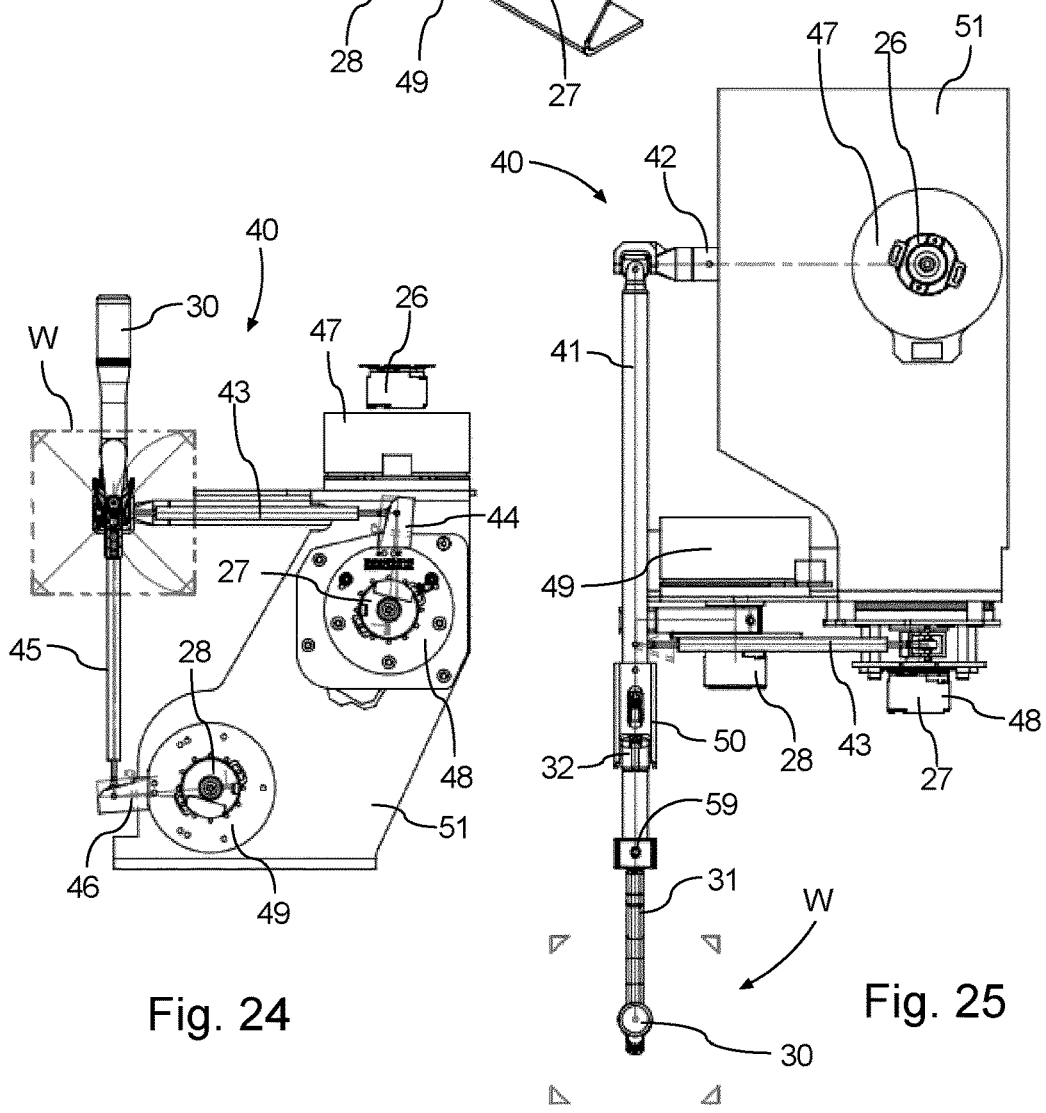
Fig. 24
Fig. 25

APPARATUSES FOR SIMULATING DENTAL PROCEDURES AND METHODS

TECHNICAL FIELD

The disclosure relates to apparatuses and methods for simulating medical and dental procedures and methods, in particular apparatuses and methods that use virtual, mixed and/or augmented reality to simulate the activities of a medical practitioner, dentist, a dental/oral/maxillofacial surgeon, dental hygienist or a dental therapist.

BACKGROUND

Dentistry, also known as Dental and Oral Medicine, is a branch of medicine that consists of the study, diagnosis, prevention, and treatment of diseases, disorders, and conditions of the oral cavity, commonly in the dentition but also the oral mucosa, and of adjacent and related structures and tissues, particularly in the maxillofacial (jaw and facial) area. Dentistry encompasses practices related to the oral cavity, as performed by dentists, dental surgeons, oral surgeons, maxillofacial surgeons, dental hygienists, and dental therapists in the form of dental procedures and treatments.

Dental students require facilities for training, and using real patients has obvious drawbacks.

Dental simulators for simulating dental procedures are known in the art. These simulators are used to train dentistry students thereby reducing the need for training on plastic phantom heads with plastic phantom teeth (which do not provide an accurate simulation, do not allow for objective assessment or tracking of work, and are not environment-friendly) and reducing the need for training on real patients. Known dental simulators comprise a computer which controls the simulation and hosts a virtual environment, a display screen displaying the simulated environment, and one or two handpieces connected to the computer to provide input. The simulated environment comprises the subject, a set of virtual teeth, virtual versions of tools controlled by the handpieces, as well as a virtual version of the handpieces themselves. The tools may be surgical instruments (scalpels, syringes, etc.) or other devices (such as mirrors or probes). The handpieces are connected to sensors that determine their position and orientation, which is used to control (display) the position of the tools in the virtual environment. Typically, one of the handpieces is mounted on a haptic feedback system through which the computer controls the forces the user feels through the handpiece.

A static U-shaped rail or the like serves as a handrest for the hands/fingers of the dentistry student (user). In real dental procedures or treatments, the dentist will typically rest his fingers on the patient's teeth and jaw, and a simulation with a single fixed U-shaped rail in the known dental simulator is therefore not a realistic simulation.

The visual display screen is disposed between the user's eyes and the handpieces and the rail and presents a virtual environment that shows a virtual set of teeth on a virtual jaw. The known simulator comprises a computer that controls the simulation and hosts a virtual environment, a display screen displaying the simulated environment, and one or two handpieces, which are connected to the computer to provide an input/output. The simulated environment comprises the subject, as well as virtual versions of tools controlled by the handpieces. The tools may be surgical instruments (scalpels, syringes, etc.) or other devices (such as mirrors or probes). The handpieces are connected to sensors that determine their position, which is used to control the position of the tools in the virtual environment. One of the handpieces is mounted on a haptic feedback system which allows the computer to control the forces the user feels through the handpieces, making a more realistic simulation possible. Thus, a virtual version of the handpieces is displayed on the display screen, but the user cannot see his or her own fingers or hands, which is a drawback since it denies the user an important visual input.

SUMMARY

The aspects of the disclosed embodiments are directed to a dental simulator that overcomes or at least reduces at least one of the problems mentioned above.

The foregoing and other objects are achieved by the features of the independent claims. Further implementation forms are apparent from the dependent claims, the description, and the figures.

According to a first aspect, there is provided a dental procedure simulator comprising a support structure, a display screen, a computer configured to simulate a dental procedure or treatment, a linkage suspended from the support structure, the linkage being controlled by the computer to simulate a medical procedure or treatment by providing haptic force feedback, a handpiece operably coupled to the linkage and configured to be held in a hand of a user and to be manipulated by the user in a workspace in real space, a phantom upper jaw and a phantom lower jaw supported by the support structure and arranged in the workspace, the phantom lower jaw preferably being arranged movably relative to the phantom upper jaw, the computer being configured to display on the display screen a virtual environment comprising at least one virtual tooth co-located with the phantom upper jaw or with the phantom lower jaw.

By providing a phantom upper jaw and lower jaw, the computer simulation of the dental procedure becomes much more realistic for the user, caused by mixed reality through the presence of the upper and/or lower jaw. The presence of phantom jaws on which the user can support their hands/fingers in a way that closely mimics the way in which a dentist supports their hands/fingers on a real patient and enhances the computer simulation experience. Further, the visual presence of an upper and lower jaw gives a much more realistic representation of the work environment with a real patient and therefore provides a more realistic simulation.

According to a possible implementation form of the first aspect the phantom upper jaw and the phantom lower jaw are movable relative to the support structure, the dental procedure simulator comprising one or more sensors configured to sense the position and orientation of the phantom upper jaw and the phantom lower jaw relative to the support structure, wherein the computer is through the one more sensors in receipt of the position and orientation of the phantom upper jaw and the phantom lower jaw, and the computer being configured to adjust the orientation and position of the at least one virtual tooth to the movement of the phantom upper jaw or phantom lower jaw so that the at least one virtual tooth remains co-located on the display screen with the phantom upper jaw or phantom lower jaw when the phantom upper jaw or phantom lower jaw is moved.

According to a possible implementation form of the first aspect of the phantom upper jaw and the phantom lower jaw are manually movable by a user.

According to a possible implementation form of the first aspect, the computer is configured to display at least a portion of the virtual upper jaw and a portion of a virtual lower jaw, the computer being configured to co-locate the virtual upper jaw with the phantom upper jaw and to co-locate the virtual lower jaw with the phantom lower jaw on the display screen, also when the phantom upper jaw or the phantom lower jaw is moved.

According to a possible implementation form of the first aspect, the phantom lower jaw is suspended from the phantom upper jaw by a hinge mechanism, for example, a four-bar linkage, preferably a hinge mechanism that imitates the movement of a human jaw.

According to a possible implementation form of the first aspect, the phantom lower jaw is suspended from the phantom upper jaw to allow movement between an open position and a closed position.

According to a possible implementation form of the first aspect, the dental procedure simulator comprises a position sensor configured to create a signal indicative of the position of the phantom lower jaw relative to the phantom upper jaw.

According to a possible implementation form of the first aspect, the closed position corresponds to a position for examining the occlusal reduction.

According to a possible implementation form of the first aspect, the computer is configured to display on a display screen a set of virtual upper teeth for the phantom upper jaw and a set of lower virtual teeth for the phantom lower jaw, thereby allowing visual occlusal examination of the virtual set of teeth in the closed position.

According to a possible implementation form of the first aspect, the phantom upper jaw is suspended from the support structure to allow, rotation in one, two, or three rotational degrees of freedom, preferably with the center of rotation for each degree of freedom being located between the phantom upper jaw and the phantom lower jaw.

According to a possible implementation form of the first aspect the rotation in the one, two, or three degrees of freedom is preferably manually imparted, and wherein the dental procedure simulator comprises one or more rotary position sensors for sensing rotation of the phantom upper jaw for each of the one to three degrees of freedom.

According to a possible implementation form of the first aspect, the computer is in receipt of a signal from the one or more rotary position sensors, and wherein the computer (80) is configured to adjust the simulation of the dental procedure or treatment to the signal from the rotary position sensors.

According to a possible implementation form of the first aspect, the phantom upper jaw is suspended from the support structure by a first mechanism that allows the upper jaw to rotate about a first horizontal axis Y that is disposed in the workspace without the first mechanism intruding the workspace, the first mechanism preferably comprising a remote center linkage, preferably two spaced parallel remote center linkages.

According to a possible implementation form of the first aspect, the phantom upper jaw is suspended from the support structure by a second mechanism that allows the phantom upper jaw to rotate about a second horizontal axis that is disposed in the workspace without the second mechanism intersecting the workspace.

According to a possible implementation form of the first aspect, the phantom upper jaw is suspended from the support structure by a third mechanism that allows rotation of the phantom upper jaw about a vertical axis Z, without the third mechanism intersecting the workspace.

According to a possible implementation form of the first aspect, the phantom upper jaw comprises an upper support member with a removable upper jaw element removably attached thereto, and wherein the phantom lower jaw comprises a lower support member with a removable lower jaw element removably attached thereto.

According to a possible implementation form of the first aspect the removable upper jaw element is a generic upper jaw element, the generic upper jaw element preferably not having/defining teeth and wherein the removable lower jaw element is a generic lower jaw element, the removable lower jaw element preferably not having/defining teeth.

According to a possible implementation form of the first aspect, the removable upper jaw element is a specific upper jaw element that is provided with phantom teeth, the phantom teeth preferably being removably attached to the specific upper jaw element, the specific upper jaw element with its phantom teeth preferably being an accurate replica of a portion of a real human upper jaw with its teeth and wherein the removable lower jaw element is a specific lower jaw element that is provided with phantom teeth, the phantom teeth preferably being removably attached to the specific lower jaw element and the specific lower jaw element with its phantom teeth preferably being an accurate replica of a portion of a real human lower jaw with its teeth.

According to a possible implementation form of the first aspect, the computer is provided with a virtual model of the specific upper jaw element and/or of the specific lower jaw element.

According to a possible implementation form of the first aspect, the phantom upper jaw and phantom lower jaw are part of a phantom head, the phantom head with its phantom lower jaw, and phantom upper jaw preferably being configured to move in unison with one another.

According to a possible implementation form of the first aspect, the computer is configured to instruct a user to install/remove a specific upper or lower jaw element on/from a support member, the computer preferably also being configured to instruct the user to insert/remove a phantom tooth in/from a specific jaw element.

According to a possible implementation form of the first aspect, the computer is coupled to a display screen, and wherein the dental procedure simulator is configured to project an image from the display screen via a partially transparent reflective element to the eyes of a user whilst allowing the user a view of the workspace, the handpiece, the phantom upper jaw, and the phantom lower jaw through the partially transparent reflective element.

According to a possible implementation form of the first aspect the computer is configured to simulate the medical or dental procedure or treatment through force feedback in response to manipulation of the and handpiece by the user in the workspace.

According to a possible implementation form of the first aspect, the phantom upper jaw and/or the phantom lower jaw is a segmented phantom jaw, in which at least one of the segments is removable.

By using a segmented phantom jaw, in which at least one or more or all of the segments can be removed, and of course also be reinstalled, it is possible to avoid abutment between the haptic arm and the phantom jaw, which can occur especially for activities that relate to simulated treatment of virtual teeth associated with the lower jaw. In other words, in some situations, a portion of the phantom jaw is in the way for the haptic arm, and by removing the section of the segmented phantom jaw concerned, place is made for the haptic arm, whilst most of the phantom jaw is still present for the user to use as support for their hands and for providing realism to the simulation.

According to a second aspect, there is provided a dental procedure simulator comprising:

a support structure, a computer configured to simulate a dental procedure or treatment, a linkage suspended from the support structure, the linkage being controlled by the computer to simulate a medical procedure or treatment by providing haptic force feedback that is configured to simulate a dental procedure or treatment, a handpiece operably coupled to the linkage and configured to be held in a hand of a user and to be manipulated by the user in a workspace in real space, a phantom upper jaw movably supported by the support structure and arranged in the workspace, wherein the phantom upper jaw is suspended from the support structure by a mechanism that allows the phantom upper jaw to rotate about at least one axis that is disposed in the workspace without the mechanism intersecting the workspace.

By providing a linkage that does not intrude to the workspace it's possible to use a phantom head in a computer simulation of a dental procedure or treatment that does not interfere with the workspace required for movement of the handpiece.

According to a possible implementation form of the second aspect, the phantom upper jaw is suspended from the support structure by a first mechanism that allows the upper jaw to rotate about a horizontal axis that is disposed in the workspace without the first mechanism intruding the workspace, the first mechanism preferably comprising at least one spaced parallel remote center linkage.

According to a possible implementation form of the second aspect, the phantom upper jaw is suspended from the support structure by a second mechanism that allows rotation of the phantom upper jaw about a horizontal axis, without the second mechanism intersecting the workspace, the second mechanism preferably comprising an L-shaped plate that extends between the phantom head and the phantom upper jaw.

According to a possible implementation form of the second aspect, the phantom upper jaw is suspended from the support structure by a third mechanism that allows rotation of the phantom upper jaw about a vertical axis, without the third mechanism intersecting the workspace, the third mechanism preferably comprising a hinge pin that connects the first mechanism to an L-shaped plate and allows the L-shaped plate to rotate about a vertical axis.

According to a third aspect, there is provided an apparatus for simulating or training a dental procedure or treatment, the apparatus comprising: a handpiece configured to be held in a hand of a user and to be manipulated by the user in a workspace in real space, a haptic arm controlled by a computer that is configured to simulate a dental procedure or treatment, the handpiece being mechanically connected to the haptic arm, a powered dental handpiece with a motor for driving a dental burr, a support for supporting at least one phantom tooth in the workspace.

By providing both a handpiece for computer simulation of the dental procedure or treatment and a handpiece for physical simulation of the dental procedure, both types of training can be performed by a single machine, thereby providing significant cost and space savings.

According to a possible implementation form of the third aspect, the powered dental handpiece is provided with electrical or pneumatic power via a cable connected to the powered dental handpiece.

According to a possible implementation form of the third aspect, the apparatus comprises at least one phantom jaw for supporting the at least one phantom tooth.

According to a possible implementation form of the third aspect, the phantom teeth are at least partially made of a polymer material.

According to a possible implementation form of the third aspect, the computer has at least a first mode of operation for simulating a dental procedure or treatment using the handpiece and a second mode of operation for training a dental procedure or treatment using the powered dental handpiece.

According to a possible implementation form of the third aspect, the handpiece is a passive handpiece that does not comprise any motor and is not configured to operate a dental burr.

According to a fourth aspect, there is provided a medical procedure simulator comprising: a handpiece configured to be held in a hand of a user and to be manipulated by the user in a workspace in real space, and a linkage controlled by a computer that is configured to simulate a medical procedure or treatment, the linkage comprising an elongated main link, a first crank, a second crank and a third crank, a first actuator driving the first crank, a second actuator driving the second crank, a third actuator driving the third crank, the handpiece being connected to an extremity of the main link by a mechanical joint, the first crank being arranged to actuate the main link in a longitudinal direction, the second crank being arranged to actuate the main link in a first transverse direction, and the third crank being arranged to actuate the main link in a second transverse direction different from the first transverse direction, the first crank being coupled directly to the main link by a second mechanical joint, the second crank being coupled to the main link by a first connecting rod, the first connecting rod being coupled at a first end to the second crank and the first connecting rod being coupled at a second end to the main link, and the third crank being coupled to the main link via a second connecting rod, the second connecting rod being coupled at a first end to the third crank and the second connecting rod being coupled at a second end to the main link.

The linkage of the medical procedure simulator is uncomplicated and therefore reliable and inexpensive since it contains a relatively low number of components. Further, the linkage is suitable to provide a cuboid workspace with the sides of the workspace being vertical and horizontal.

In a first possible implementation form of the fourth aspect, the first crank is connected to the main link at a first axial position, the first connecting rod is coupled to the main link at a second axial position between the extremity and the first axial position and the second connecting rod is coupled to the main link at a third axial position between the extremity and the first position, the second and third axial position preferably being substantially identical.

In a second possible implementation form of the fourth aspect, the main link comprises a three-dimensional force sensor for sensing forces applied by the user to the handpiece in three dimensions, the three-dimensional force sensor being disposed between the extreme position and the second and/or third axial position, and the three-dimensional force sensor preferably being an integral part of the main link.

In a third possible implementation form of the fourth aspect, the first, second, and/or third cranks are coupled to a rotary position sensor or encoder.

In a fourth possible implementation form of the fourth aspect, the first, second, and/or third actuators are rotary actuators.

In a fifth possible implementation form of the fourth aspect, the respective rotation axes of the first, second, and third cranks are arranged orthogonally relative to one another.

In a sixth possible implementation form of the fourth aspect the first connecting rod extends substantially horizontally, the second connecting rod extends substantially vertically, and the rotation axis of the first crank extends substantially vertically.

In a seventh possible implementation form of the fourth aspect, the computer is configured to simulate a medical procedure or treatment through haptic feedback, preferably haptic force control feedback, with the linkage and through visual feedback with a display screen.

In an eighth possible implementation form of the fourth aspect the medical procedure simulator comprising a reference, wherein the first, second, and third cranks are mounted on the reference.

In a ninth possible implementation form of the fourth aspect, the medical procedure simulator comprises a reference, wherein the linkage provides at least six independent degrees of freedom for the handpiece relative to the reference.

In a tenth possible implementation form of the fourth aspect, the linkage connects the handpiece to the reference.

In an eleventh possible implementation form of the fourth aspect, the handpiece comprises an inertial measurement unit, the inertial measurement unit preferably being configured to create orientation data indicative of the rotational orientation of the handpiece, preferably the rotational orientation of the handpiece in real space and/or relative to the reference.

In a twelfth possible implementation form of the fourth aspect, the free end of the first crank is coupled to the main link, preferably by a mechanical joint that offers relative movement between the main link and the first crank with at least two degrees of freedom, such as for example a universal joint.

In a thirteenth possible implementation form of the first aspect, the second transverse direction is substantially perpendicular to the first transverse direction.

In a fourteenth possible implementation form of the fourth aspect, the computer is configured to simulate the medical procedure or treatment by using the signal from the three-dimensional force sensor as input and by controlling the velocity of the extremity accordingly.

According to a fifth aspect, there is provided a medical procedure simulator comprising a handpiece coupled to a haptic force feedback system that provides haptic force feedback, the force feedback system comprising at least one actuator, the control system comprising a virtual model configured to calculate a virtual force and a force sensor configured to sense the force applied to the handpiece, the virtual model being in receipt of a signal representative of the velocity of the handpiece, a summing point summing the virtual force and the sensed force, a lead-lag compensator receiving the output of the summing point, a PI or PID controller receiving the output of the lag-lead compensator, a motor drive in receipt of a velocity command from the PI or PID controller, the at least one actuator being electrically driven by the motor drive.

By using a lead-lag compensator in a medical procedure simulator, high frequencies resulting from contact instability or system resonances are removed from the input signal to the PI or PID controller resulting in a more stable smooth operation of the medical procedure simulator with a realistic feel.

In a possible implementation of the fifth aspect, the virtual model is in receipt of a signal that is indicative of the orientation of the handpiece 30.

In another possible implementation of the second aspect, the virtual model is in receipt of a signal that is indicative of the rotational speed of the virtual burr.

According to a sixth aspect, there is provided a dental procedure simulator comprising a computer configured to simulate a dental procedure or treatment, a handpiece configured to be held in a hand of a user and to be manipulated by a user in a workspace in real space, the computer being configured to generate images of the simulated dental procedure for display on a display screen, a partially transparent reflective element arranged to reflect an image on the display screen to the eyes of the user, the workspace being arranged to be visible for the user through the partially transparent reflective element.

By providing a partially transparent reflective screen it becomes possible for a user to see their own hands while training for the medical procedure. This is an important visual feedback that greatly enhances the user experience. The resulting mixed reality enhances the overall user experience.

According to a sixth possible implementation of the first aspect, the dental procedure simulator is configured to reflect the images from the display screen to the eyes of the user by reflection on the partially transparent reflective element and configured to mix the images with a view of the workspace (W) seen by the user through the partially transparent reflective element.

According to a first possible implementation of the sixth aspect, the images on the display screen are reflected to the eyes of the user, and wherein the workspace is simultaneously visible for the user through the partially transparent reflective element when the user looks at the partially transparent reflective element from a viewing space.

According to a third possible implementation of the sixth aspect, the display screen is a stereoscopic display screen.

According to a fourth possible implementation of the sixth aspect, the computer is configured to send stereoscopic images to the stereoscopic display screen.

According to a fifth possible implementation of the sixth aspect, the stereoscopic display screen is an autostereoscopic display screen.

According to a sixth possible implementation of the sixth aspect, the computer is configured to produce images of a virtual handpiece co-located with the handpiece, the images preferably being stereoscopic images.

According to a seventh possible implementation of the sixth aspect, the computer is configured to provide a three-dimensional virtual environment comprising a first virtual tool having a first virtual position and a first virtual orientation, the first virtual tool corresponding in size and shape to the handpiece and the first virtual tool being co-located with the handpiece.

According to an eighth possible implementation of the sixth aspect, the partially transparent reflective element is a partially transparent mirror or a semi-transparent mirror.

According to a ninth possible implementation of the sixth aspect, the dental procedure simulator is provided with adjustable lighting on the workspace.

According to a tenth possible implementation of the sixth aspect, the dental procedure simulator is provided with a phantom upper jaw and a phantom lower jaw, both disposed in the workspace.

According to an eleventh possible implementation of the sixth aspect, the dental procedure simulator is provided with a phantom head disposed in the workspace, the phantom head preferably comprising the phantom upper jaw and the phantom lower jaw.

According to a seventh aspect, there is provided a method of simulating a dental procedure or treatment comprising: providing a dental procedure simulator comprising a handpiece configured to be held in a hand of a user and to be manipulated by a user in a workspace in real space, generating images of a virtual environment with the simulated dental procedure or treatment on a display screen, reflecting the images to a user via a partially transparent reflective element, and allowing the user to simultaneously view the workspace through the partially transparent reflective element and the images of the virtual environment through reflection by the partially transparent reflective element.

According to a first possible implementation of the seventh aspect, the workspace comprises at least one movable phantom jaw and/or movable phantom head and wherein the virtual environment comprises at least one virtual jaw with a virtual tooth, and the method comprises adjusting the position of the virtual jaw with virtual teeth to maintain co-location with the phantom jaw.

According to an eighth aspect, there is provided a dental procedure simulator comprising:

a computer configured to simulate a dental procedure or treatment, a parallel robot controlled by the computer, the parallel robot providing at least three degrees of translative freedom, the parallel robot being controlled by the computer to simulate a dental procedure or treatment by providing haptic force feedback through the parallel robot, a handpiece operably coupled to the parallel robot by a mechanism that provides at least three degrees of rotational freedom, the handpiece being configured to be held in a hand of a user and to be manipulated by a user in a workspace in real space, and an autostereoscopic display screen, the computer being configured to generate stereoscopic images of the simulated dental procedure for display on the autostereoscopic display screen, and the computer being configured to generate stereoscopic images of a virtual handpiece co-located with the handpiece.

By providing a dental procedure simulator with a force feedback parallel robot, combined with an autostereoscopic display, it is possible to provide highly realistic training for dental practitioners or students, without the trainees needing to use 3D (shutter) glasses.

According to a possible implementation form of the eighth aspect, the dental procedure simulator comprises a parallel robot controlled by the computer, the parallel robot providing at least three degrees of translative freedom, the parallel robot being controlled by the computer to simulate a dental procedure or treatment by providing haptic force feedback through the parallel robot, the handpiece being operably coupled to the parallel robot by a mechanism that provides at least three degrees of rotational freedom.

According to a possible implementation form of the eighth aspect, the parallel robot comprises one actuator for each degree of translative freedom.

According to a possible implementation form of the eighth aspect, the dental procedure simulator comprises sensors for sensing the orientation of the handpiece.

According to a possible implementation form of the eighth aspect, the dental procedure simulator comprises a partially transparent reflective element arranged to reflect an image from the autostereoscopic display screen to the eyes of the user, the workspace being arranged to be visible for the user through the partially transparent reflective element.

According to a possible implementation form of the eighth aspect the computer is configured to generate a three-dimensional virtual environment comprising a first virtual tool having a first virtual position and a first virtual orientation, the first virtual tool preferably corresponding in size and shape to the handpiece and the computer being configured to co-locate the first virtual tool with the handpiece.

According to a ninth aspect, there is provided a dental procedure simulator comprising a computer that is configured to simulate a dental procedure or treatment, a reference, a first handpiece simulating a dental drill, the first handpiece being configured to be held in a hand of a user and to be manipulated by the user in a workspace in real space, a linkage coupled to the reference, the linkage being control controlled the computer that is configured to simulate a dental procedure or treatment by providing haptic feedback through the linkage, a second handpiece for simulating a dental mirror, the second handpiece being configured to be held in a hand of a user and to be manipulated by the user in a workspace in real space, a primary link coupled to the reference by one or more joints that provide a first and second degree of freedom, a secondary link coupled to the primary link by one or more joints that provide a third and fourth degree of freedom, the second handpiece being connected to the secondary link by one or more joints that provide a fifth and sixth degree of freedom to form a serial chain that connects the second handpiece to the reference with six degrees of freedom, a first sensor for sensing movement in the first degree of freedom, a second sensor for sensing movement in the second degree of freedom, a third sensor for sensing movement in the third degree of freedom, the first, second and third position sensors being in data connection with the computer, and an inertial measurement unit arranged in the second handpiece, the inertial measurement unit being in data connection with the computer and the inertial measurement unit being configured to sense movements in at least the fourth, fifth and sixth degrees of freedom.

The combination of three position sensors with the inertial measurement unit in the handpiece provides for a relatively uncomplicated but still accurate system for determining the exact position of the handpiece relative to a reference since the signal from the position sensors can be used to compensate for drift of the inertial measurement unit.

In a first possible implementation form of the ninth aspect the handpiece is connected to the secondary link by one or more joints that provide a sixth degree of freedom, the sixth degree of freedom allowing the handpiece to rotate about an axis of the handpiece and the inertial measurement unit being configured to sense the sixth degree of freedom.

In a second possible implementation form of the ninth aspect first sensor, the second sensor or the third sensor are rotary position sensors.

In a third possible implementation form of the ninth aspect, the primary link is an elongated link that is coupled to the reference by a third pivot joint that allows the primary link to rotate about its longitudinal axis to realize the first degree of freedom.

In a fourth possible implementation form of the ninth aspect, the first sensor is a rotary position sensor configured to sense rotation about the longitudinal axis of the primary link.

In a fifth possible implementation form of the ninth aspect, the primary link s an elongated link that is coupled to the reference by a hinge that allows the primary link to rotate about a transverse axis to obtain the second degree of freedom.

In a sixth possible implementation form of the ninth aspect, the second position sensor is a rotary position sensor configured to sense rotation of the primary link about the transverse axis.

In a seventh possible implementation form of the ninth aspect, the secondary link is an elongated link that is coupled to the primary link by a third hinge that allows the secondary link to rotate about a transverse axis to obtain the third degree of freedom.

In an eighth possible implementation form of the ninth aspect, the third sensor is a rotary position sensor configured to sense rotational movement of the secondary link about the transverse axis.

In a ninth possible implementation form of the ninth aspect, the secondary link is an elongated link that is coupled to the primary link by a second pivot joint that allows the secondary link to rotate about its longitudinal axis to obtain the fourth degree of freedom.

In a tenth possible implementation form of the ninth aspect, the medical procedure simulator comprises a tertiary link coupled to a quaternary link, the tertiary link being coupled to the primary link or to the secondary link, and the quaternary link being coupled to the third sensor to form a serial chain that translates rotation of the secondary link about the transverse axis of the secondary link into rotational movement of the third sensor.

In an eleventh possible implementation form of the ninth aspect, the medical procedure simulator comprises a second hinge to provide a fifth degree of freedom for the handpiece.

In a twelfth possible implementation form of the ninth aspect, the medical procedure simulator comprises a fourth pivot joint that allows the handpiece to rotate about an axis of the handpiece to provide a sixth degree of freedom.

In a thirteenth possible implementation form of the ninth aspect, the medical procedure simulator comprises a rotary position sensor inside the handpiece for sensing rotation of the handpiece about the axis of the handpiece.

In a fourteenth possible implementation form of the ninth aspect, the inertial measurement unit is configured to sense rotation of the handpiece about the axis of the handpiece.

In a fifteenth possible implementation form of the ninth aspect, the inertial measurement unit is configured to sense movement in up to six degrees of freedom, preferably three degrees of rotational freedom and wherein the computer is configured to use the signal from the first, second and or third sensors as a reference for calibrating the inertial measurement unit.

According to a tenth aspect, there is provided a medical procedure simulator comprising: a handpiece configured to be held in a hand of a user and to be manipulated by the user in a workspace in real space, a linkage controlled by a computer that is configured to simulate a medical procedure or treatment, the handpiece comprising an inner part extending into an outer part with the outer part being configured to rotate about the inner part, a portion of the inner part protrudes from the outer part, the portion being coupled to the linkage by a joint with at least two degrees of freedom, an inertial measurement unit mounted to the inner part and coupled to the computer, and a rotary position sensor for sensing rotational movement of the outer part relative to the inner part, the rotary position sensor being coupled to the computer, at least a first portion of the rotary position sensor being mounted on the inner part, and the first portion being connected to the computer by a cable that is guided or supported by the inner part.

The inner part and outer part arrangement of the handpiece results in increased degrees of freedom for the user operating the handpiece with his or her hand. The arrangement with at least a first part of the rotation sensor being mounted on the inner part allows infinite rotation of the outer part relative to the inner part, providing the handpiece with infinite rotation about its longitudinal axis. Since the rotary position sensor can be at least partially arranged on the inner part, it is possible to connect the rotary sensor to the computer by cable without the need for slip rings or the like to allow rotation, since the cable is not exposed to rotation. Not having slip rings or the like in the connection between the rotary position sensor and the computer provides a more reliable connection between the rotary position sensor and the computer.

In a first possible implementation form of the tenth aspect, the inertial measurement unit is configured to create orientation data indicative of the rotational orientation of the handpiece.

In a second possible implementation form of the tenth aspect, the inertial measurement unit is coupled to the computer by a cable that is guided or supported by the inner part.

In a third possible implementation form of the tenth aspect, the medical procedure simulator comprises a first rotary bearing between the inner part and the outer part and preferably a second rotary bearing, axially spaced from the first rotary bearing.

In a fourth possible implementation form of the tenth aspect, the outer part is arranged to rotate about a longitudinal axis of the inner part.

In a fifth possible implementation form of the tenth aspect, the inner part is elongated and is connected to the joint at a first extremity of the inner part, the rotary position sensor being arranged at or near a second extremity of the inner part, the second extremity being located inside the outer part.

In a sixth possible implementation form of the tenth aspect, the inertial measurement unit is configured for creating position and/or orientation data of the handpiece in real space, preferably relative to a reference.

In a seventh possible implementation form of the tenth aspect, the coupling of the inertial measurement unit to the computer comprises a data link from the inertial measurement unit to the computer for transmission of position and/or orientation data.

In an eighth possible implementation form of the tenth aspect, the coupling of the rotary position sensor to the computer comprises a data link from the rotary position sensor to the computer for transmission of rotary position data.

In a ninth possible implementation form of the tenth aspect, the outer part has infinite rotation relative to the inner part.

In a tenth possible implementation form of the tenth aspect, the longitudinal extent of the outer part comprises a proximate portion and a distal portion extending at an angle to the proximate portion, with the inner part protruding from the outer part through the distal portion.

According to an eleventh aspect, there is provided a dental procedure simulator with a front side and a rear side, the dental procedure simulator comprising: a computer that is configured to simulate a dental procedure or treatment, a linkage controlled by the computer, a handpiece coupled to the linkage and configured to be held in a hand of a user and to be manipulated by the user in a workspace in real space, a display screen coupled to the computer for displaying images generated by the computer, a base, a main structure with a substantially flat bottom, the linkage being at least partially received in the main structure, and a post that supports the main structure above the base with a distance between the substantially flat bottom and the base to create a space between the substantially flat bottom and the base, the post being height adjustable for changing the distance between a surface on which the base is placed and the substantially flat bottom to a range that preferably comprises at least distances between 70 and 80 cm, more preferably at least distances between 65 and 85 cm, the post (3) being disposed laterally offset relative to the base and relative to the substantially flat bottom, the post extending from a position adjacent a front side of the base, preferably at the front side of the base, to a position adjacent a front side of the main structure, preferably at the front side of the main structure.

The space between the substantially flat bottom and the base allows the dental procedure simulator to take up less space as it can easily be fitted to different room settings. Particularly, the substantially flat bottom of the main housing and the height adjustability of the post allows the main housing to be arranged e.g. over a worktop or desktop, thereby saving valuable room space.

In a first possible implementation form of the eleventh aspect, the space between the base and the flat bottom is an empty space only intersected by the post.

In a second possible implementation form of the eleventh aspect, the space is accessible from all lateral directions except where access is barred by the post.

In a third possible implementation form of the eleventh aspect, the dental procedure simulator comprises two or more posts, wherein the two or more posts are all disposed laterally offset to one and the same side of the base and of the main housing.

In a fourth possible implementation form of the eleventh aspect, the main housing is only supported by one post.

In a fifth possible implementation form of the eleventh aspect, the space is open to the environment except where the space is shielded by the base, the substantially flat bottom, or the post.

In a sixth possible implementation form of the eleventh aspect, the post is height adjustable for changing the distance between the base and the substantially flat bottom, preferably a motorized height adjustable post.

In a seventh possible implementation form of the eleventh aspect, the post comprises a linear actuator for height adjustment.

In an eighth possible implementation form of the eleventh aspect, the display screen is arranged in a display housing that is disposed above the main housing, the display housing preferably being supported above the main housing by an arm that is connected to the post or to the main housing.

In a ninth possible implementation form of the eleventh aspect, the base comprises a lower housing.

In a tenth possible implementation form of the eleventh aspect, the main housing comprises a reference for supporting the linkage.

In an eleventh possible implementation form of the eleventh aspect, the base is configured for resting on a floor and the base is preferably wheeled.

In a twelfth possible implementation form of the eleventh aspect, the computer is configured to generate images of the simulated dental procedure or treatment for displaying on the display screen.

In a thirteenth possible implementation form of the eleventh aspect, the post extends from the base to the main housing.

In a fourteenth possible implementation form of the eleventh aspect, the post extends from a position adjacent to a lateral side of the base to a position adjacent to a lateral side of the main housing.

These and other aspects will be apparent from and the embodiment(s) described below.

BRIEF DESCRIPTION OF THE DRAWINGS

In the following detailed portion of the present disclosure, the aspects, embodiments, and implementations will be explained in more detail with reference to the example embodiments shown in the drawings, in which:

FIGS. 23 to 26 are elevated and isometric views, respectively of an embodiment of a linkage with its drive system and a handpiece that is connected to the linkage.

DETAILED DESCRIPTION

Figure 1:
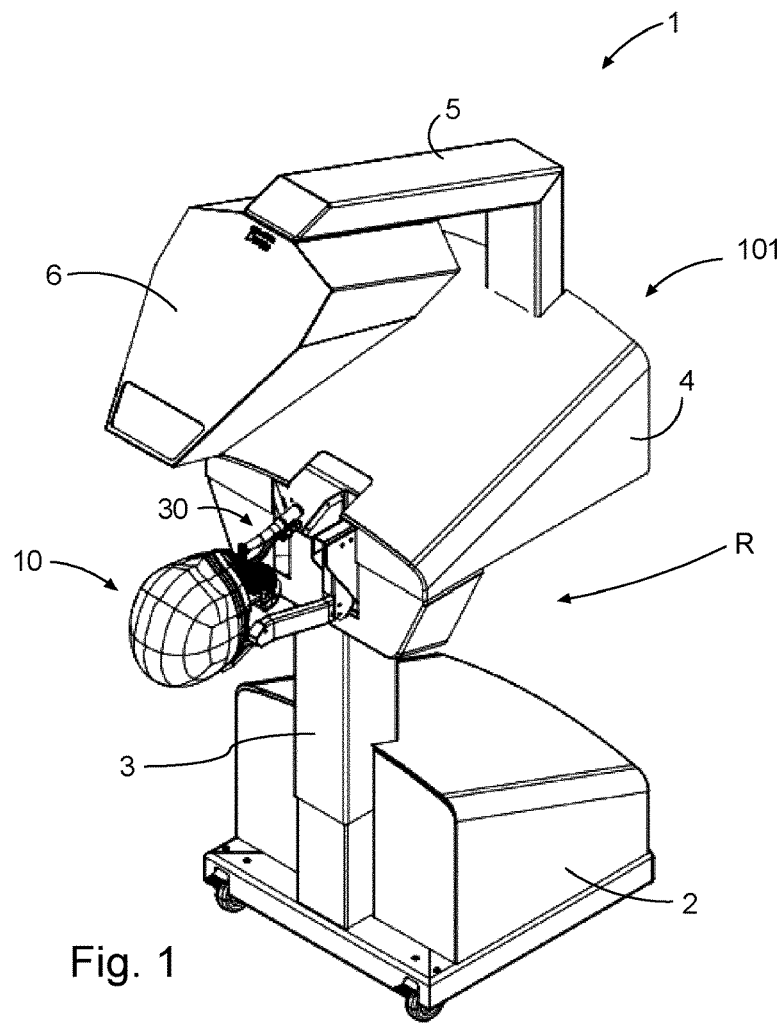
FIG. 1 is an elevated view of a dental procedure simulator according to an embodiment.

Referring to the drawings, and particularly to FIGS. 1 to 7 and 34 which show a first embodiment of a medical procedure simulator 1, in particular, a dental procedure simulator 1 for simulating dental procedures and treatments. The medical procedure simulator 1, is intended to be used to train the skills and competences of medical professionals or students. In case of a dental procedure simulator 1, the dental procedure simulator is intended to be used to train the skills and competences of dentists, dental surgeons, oral surgeons, maxillofacial surgeons, dental hygienists, and dental therapists. The users that undergo training with the dental procedure simulator can be students or professionals. The dental procedure simulator 1 generally includes a first handpiece 30, in this embodiment a first handpiece 30 that represents a dental drill handle, a base 2, in this embodiment a base with a lower housing that houses a computer 80, a post 3, in this embodiment a height-adjustable column, a main housing 4 that houses a linkage 40 to which the first handpiece 30 is connected, a phantom head 10, and a support arm 5 supporting a display housing 6.

The base 2 is in an embodiment a wheeled base for allowing the medical procedure simulator 1 to be easily rolled by a user to another position. The post 3 extends from the base 2 to the main housing 4 and supports the main housing 4 above the base 2 with a distance between a substantially flat bottom of the main housing 4 and the base 2 to create a space R between the substantially flat bottom and the base 2. The post 3 is disposed laterally offset relative to the base 2 and relative to the substantially flat bottom to allow the space R to be accessible from all sides (except the side where the post 3 is arranged). In an embodiment, the post 3 extends from a position adjacent a lateral side (front side) of the base 2 to a position adjacent to a lateral side (front side) of the main housing 4.

The space R between the base 2 and the flat bottom is an empty space R only intersected by the post 3. The space R is accessible from all lateral directions except where access is barred by the post 3.

In an embodiment (not shown) the dental procedure simulator 1 comprises two or more posts 3 which are all disposed laterally offset to one and the same side of the base 2 and of the main housing 4. In the shown embodiment the main housing 4 is only supported by one post 3. The space R is open to the environment except where the space R is shielded by the base 2, the substantially flat bottom, or the post 3.

Figures 2, 3:
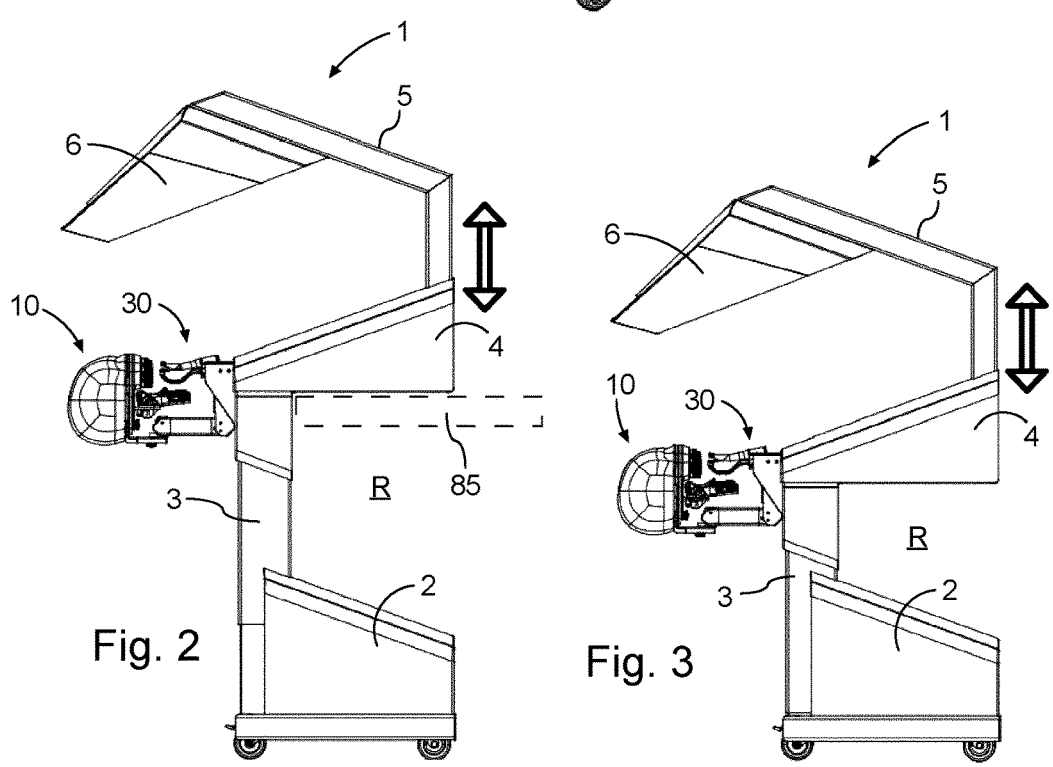
FIG. 2 is a side view of the dental procedure simulator of FIG. 1 in a first height.
FIG. 3 is a side view of the dental procedure simulator of FIG. 1 in a second height that is lower than the first height.
Figure 4:
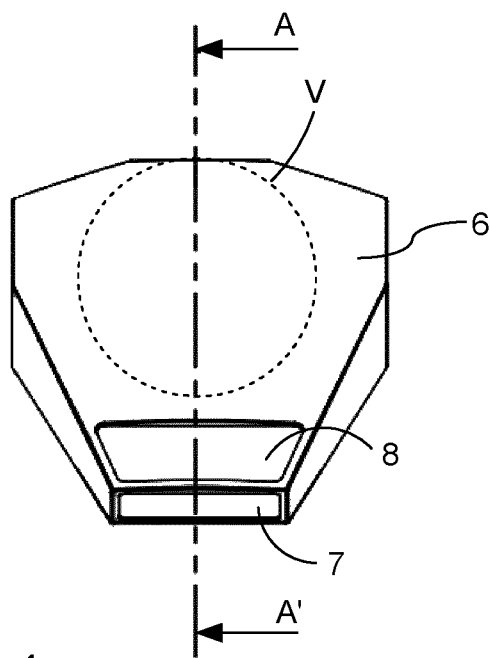
FIG. 4 shows a frontal view of a display housing of the dental procedure simulator of FIG. 1, FIG. 5. is a sectional view through the display housing of FIG. 4, also illustrating a workspace, the eye of a user, and a vision space.
Figure 5:
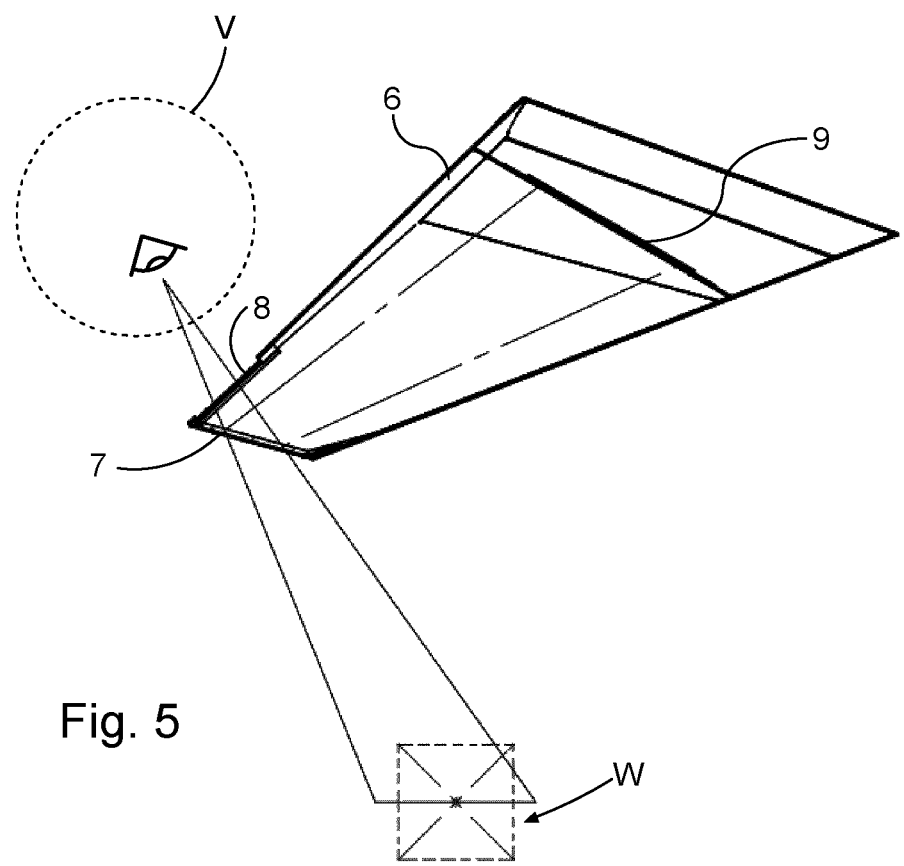
Figure 6:
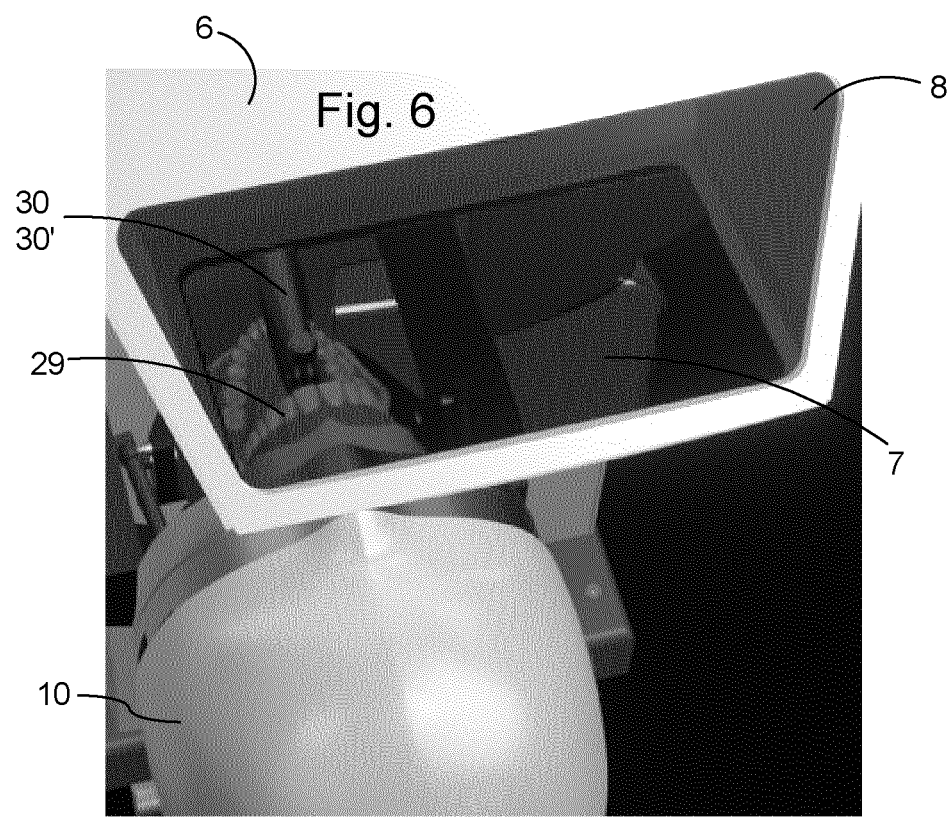
FIG. 6 is an elevated view from a user perspective through a semi-transparent mirror in the display housing to a workspace of the dental procedure simulator of FIG. 1, also showing a virtual environment through reflection from the semi-transparent mirror.
Figure 7:
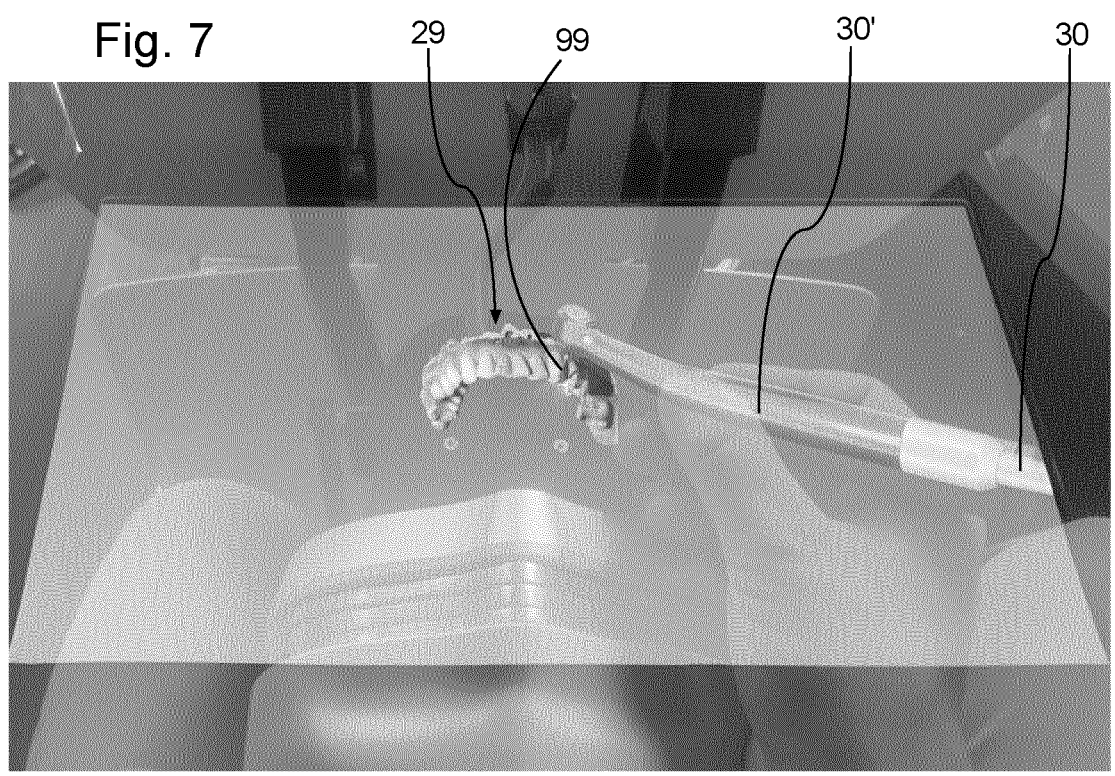
FIG. 7 is an image of a mixed reality virtual environment displayed by the dental procedure simulator of FIG. 1, FIGS. 8 to 11 are elevated views of specific phantom jaws that are used in the dental procedure simulator of FIG. 1.
Figure 8:
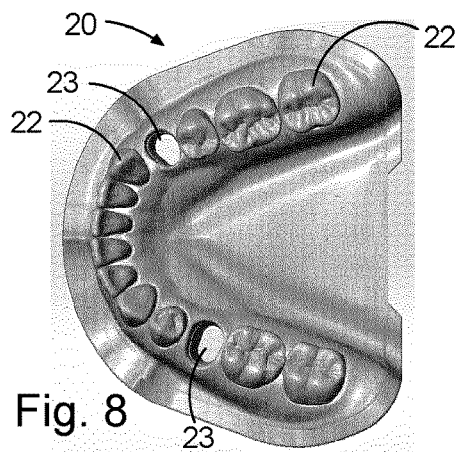
Figure 10:
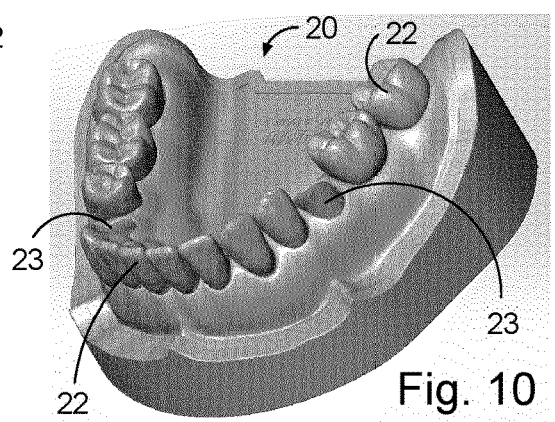
Figure 9:
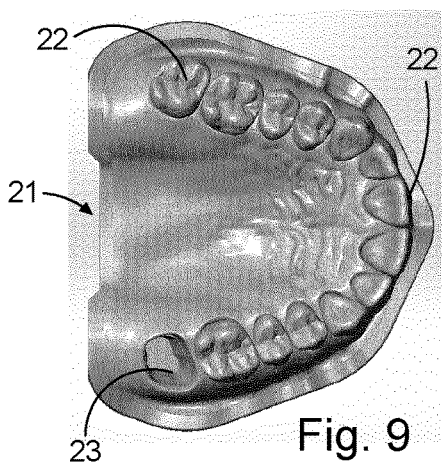
Figure 11:
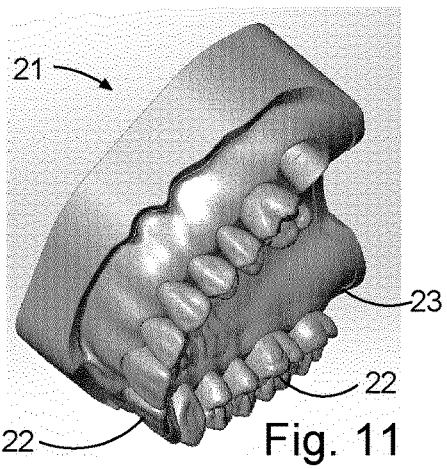
Figure 14:
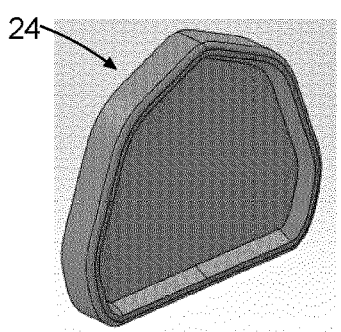
Figure 12:
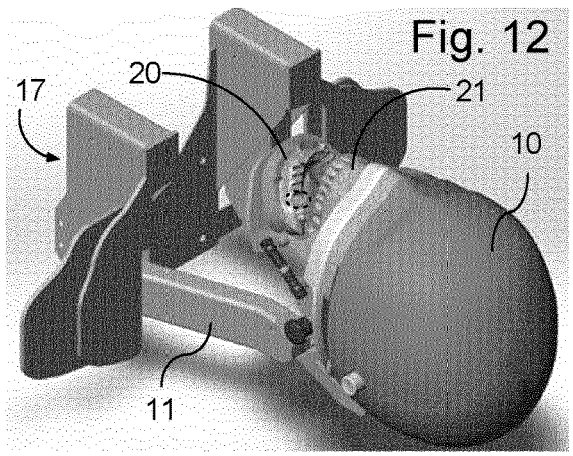
FIG. 12 is an elevated view of a phantom head and its mount system, using a lower specific phantom jaw and a specific phantom upper jaw.
Figure 15:
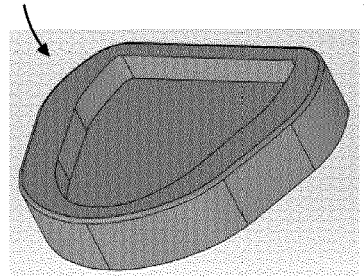
Figure 13:
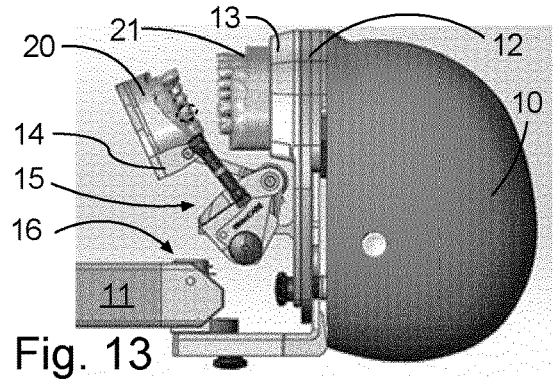
FIG. 13 is a side view of the phantom head of FIG. 12, FIGS. 14 and 15 are elevated views of generic phantom jaws that are used in the dental procedure simulator of FIG. 1.

The height of the main housing 4 is adjustable as indicated by the double-lined arrows in FIGS. 2 and 3 by operation of the post 3, that in an embodiment is motorized, e.g. by an electric linear actuator. The post 3 supports the main structure above the base 2 with a distance between the substantially flat bottom of the main housing 4 and the base 2 to create a space between the substantially flat bottom and the base 2. The post is height adjustable for changing the distance between a surface on which the base is placed (e.g. a floor) and the substantially flat bottom to a range that preferably comprises at least distances between 70 and 80 cm, more preferably at least distances between 65 and 85 cm. The post 3 is disposed laterally offset relative to the base 2 and relative to the substantially flat bottom. The post 3 extends from a position adjacent to a front side of the base 2, preferably at the front side of the base 2, to a position adjacent to a front side of the main structure 101, preferably at the front side of the main structure 101.

A phantom head 10 is suspended from the front side of the main housing 4 and the display housing 6 is suspended from the main housing 4 by a support arm 5, so that the phantom head 10 and the display housing 6 as well as the first handpiece 30 move in unison with the main housing 4 when the height of the main housing 4 is adjusted. The main housing 4, together with the support arm 5 and the display housing 6, forms the main structure 101 to which also the phantom head 10 is attached.

The main housing 4 has a substantially flat bottom that together with the height adjustability allows the main housing 4 to be arranged over a worktop or desktop 85, as shown in FIG. 2, thereby saving valuable training room space. FIG. 3 shows the main housing in a lower position. The height adjustability also allows the working height of the dental procedure simulator 1 to be adjusted to the individual user, since the phantom head 10 and the handpiece 30 will move up and down simultaneously with the main housing 4.

The medical procedure simulator 1 comprises a lower housing on the base 2 in which a computer 80 is arranged, together with power supply for the computer 80 and other electrical components of the medical procedure simulator 1. In an embodiment, the medical procedure simulator 1 comprises more than one computer.

The computer 80 has a memory and a processor. The processor is arranged to execute software stored on the memory, in particular software configured to simulate a medical procedure or treatment, especially simulation in a training or teaching context.

The computer 80 is connected to a display screen 9, a model in a workspace W, a linkage 40 mounted to the main housing 4 and to the first handpiece 30 that is also arranged in workspace W. The linkage 40 (described in detail below with reference to FIGS. 23 to 26) is mechanically connected to the first handpiece 30. The workspace W is a three-dimensional space in the real world and the first handpiece 30 can be manipulated by a user within the space without experiencing constraints from the linkage 40 (constraints caused by the range in the orthogonal directions in real space of the extremity of the linkage to which the first handpiece 30 is connected being limited).

The model represents part of the subject (for example a phantom upper jaw 13 and lower jaw 14 with or without a set of phantom teeth and with or without a phantom head 10) and provides the necessary mechanical environment for the medical procedure or treatment to take place. For example, the surgeon/dentist can rest his/her hands on the phantom jaws/teeth/head 10, 13, 14, 22 during the procedure and thus arrest his/her hands in the same way as in a treatment of a real patient.

The velocity of the handpiece 30 is adjusted in response to the forces the user applies to the first handpiece 30 and the interaction of the virtual drill 30' with a virtual tooth of a virtual model of a jaw with teeth 29. The virtual environment includes algorithms for determining how the velocity of the virtual drill 30' should change in response to the sum of the x,y,z forces applied by a user on the first handpiece 30 (from 3DOF sensor 50) and any reaction forces from virtual contact of the virtual drill or handpiece 30' with a virtual tooth. The virtual environment uses for some aspects Newtonian physics (i.e. Force=spring constant×deflection) to model the reaction forces between the virtual drill 30' and the virtual tooth, whilst changes in the velocity of the handpiece 30 are determined using a PID control loop. The virtual tooth is assigned a hardness and rigidity. The rigidity correlates to the spring constant a tooth provides when contacted and the hardness correlates to how much work a virtual drill must do in order to drill away a volume of the virtual tooth. The position of the real drill (first handpiece) 30 is used to determine whether there is contact with the virtual tooth.

Once the virtual environment calculates the virtual force acting at the virtual drill 30', it commands this force to the PID control loop that controls the velocity of the actuators (described in detail further below) in the system to change the real world velocity of the first handpiece 30. The user senses the movement of the first handpiece 30. While the velocity of the first handpiece 30 is controlled by the dental procedure simulator 1, the orientation of the first handpiece 30 is controlled by the user. The system measures the orientation of the first handpiece 30 as controlled by a user, and in response updates the orientation of the virtual drill 30' in the virtual environment. The computer 80 is also configured to update the position of the virtual drill 30' in the virtual environment.

The movably suspended phantom head 10 is used to adjust the orientation of the virtual environment shown on display 9. The orientation of the phantom head 10 can be manually adjusted and orientation of the virtual model is adjusted accordingly, using sensors (not shown) coupled to the computer 80 that measure rotation of the phantom head 10. Thus, the phantom head 10 and the phantom jaws are co-located and linked with the virtual phantom head and virtual jaws. When the user turns the phantom head 10 the virtual head rotates in the scene, when the user changes the opening degree of the lower jaw, the virtual lower jaw adjusts its position in the virtual environment accordingly. The phantom head 10 is an intuitive control for the virtual model orientation.

The computer 80 provides an interface to the user for selecting different virtual environments procedures and treatments to be simulated and running various training software applications. The training applications monitor the interaction of a user with the virtual environment and first handpiece 30 and measure various criteria to evaluate the performance of a user.

Referring now in particular to FIGS. 4 to 7 the visual housing 6 is provided with the display screen 9 that is disposed towards the rear of the display housing 6. A viewing opening or window 8 in the upper side of the display housing 6 towards the front end of the display housing 6 allows a user to view a partially transparent reflective element 7 from a viewing area V. The partially transparent reflective element 7 is disposed in the lower side of the display housing 6 towards the front end of the display housing 6 and allows a user to see the workspace W from the viewing area V through the partially transparent reflective element 7. The partially transparent reflective element 7 is arranged to reflect an image displayed on the display screen 9 to the eyes of the user whilst the workspace W is simultaneously visible for the user through the partially transparent reflective element 7 (assuming that the eyes of the user are located in the viewing area V and the user is looking towards the partially transparent reflective element 7). Thus, in the view of the user, the virtual images of the virtual environment are mixed with images of the reality of the workspace W.

The display screen 9 and the partially transparent reflective element 7 are positioned such that the view is co-located with the position of the first handpiece 30. This allows the system to produce images of a virtual dental drill 30' that line up in the line of sight of user with real-world first handpiece 30.

The dental procedure simulator is configured to reflect the images from the display screen 9 to the eyes of a user by reflection on the partially transparent reflective element 7 and is configured to mix the images of the virtual environment with a view of the workspace (W) seen by the user through the partially transparent reflective element 7.

Thus, the images on the display screen 9 are reflected to the eyes of the user, and the workspace W is simultaneously visible for the user through the partially transparent reflective element 7 when the user looks at the semi-reflective element 7 from the viewing space V.

In an embodiment, the display screen 9 is a stereoscopic display screen and the computer 80 is configured to send stereoscopic images to the stereoscopic display screen 9. In an embodiment, the stereoscopic display screen 9 is an autostereoscopic display screen 9. In an embodiment, the display screen 9 stereoscopic display screen in which the level of stereo is adjustable so that it can be adjusted to the optimal level for a particular user.

The computer 80 is configured to provide a three-dimensional virtual environment comprising a first virtual tool 30' having a first virtual position and a first virtual orientation, the first virtual tool 30' corresponds in size and shape to the handpiece 30 and the first virtual tool 30' is co-located with the handpiece 30. The a virtual burr 99 and at least one virtual tooth is displayed as part of the 3-dimensional virtual environment. In the example in FIG. 7 a complete virtual lower jaw 29 is displayed. In embodiments, both the virtual lower jaw 29 and a virtual upper jaw is displayed.

The computer 80 sends images of the simulated dental procedure or treatment to the display screen 9. The images on the display screen are reflected to a user via a semi-transparent reflective element 7 (such as e.g. a semi-transparent mirror) to the eyes of a user (assuming that the eyes of a user are located in a vision space V and the user is facing the semi-transparent reflective element 7). The vision space is a three dimensional-space where a user can simultaneously observe the images from the display screen 9 through reflection by the semi-transparent reflective element 7 and objects in the workspace W through the semi-transparent reflective element 7.

The software is configured to present a virtual environment that includes at least one virtual object, such as a virtual tooth, all of which are viewed by a user via the partially transparent reflective element 7. The virtual environment includes a virtual tool, in this embodiment, a virtual dental drill 30' corresponding to real-world haptic drill handle 30.

In an embodiment, the dental procedure simulator 1 is provided with adjustable lighting (not shown) on the workspace W. The lighting is in an embodiment mounted to the lower side of the display housing 6 and directed to the workspace W. The adjustable lighting facilitates creating the proper balance for a given user of the image of the workspace W seen through the partially transparent reflective element 7 and the images of the virtual environment reflected from the pressure transparent reflective element 7.

Referring now particularly to FIGS. 8 to 22, a phantom upper jaw 13 and the phantom lower jaw 14 are supported by the structure of the dental procedure simulator 1 and arranged in the workspace W. The phantom lower jaw 14 is arranged (manually) movable relative to the phantom upper jaw 13. The phantom lower jaw 14 is suspended from the phantom upper jaw 13 by a hinge mechanism 15, in an embodiment a four-bar linkage. Preferably, the hinge mechanism 15 imitates the movement of a human jaw to render the model realistic.

Figure 19:
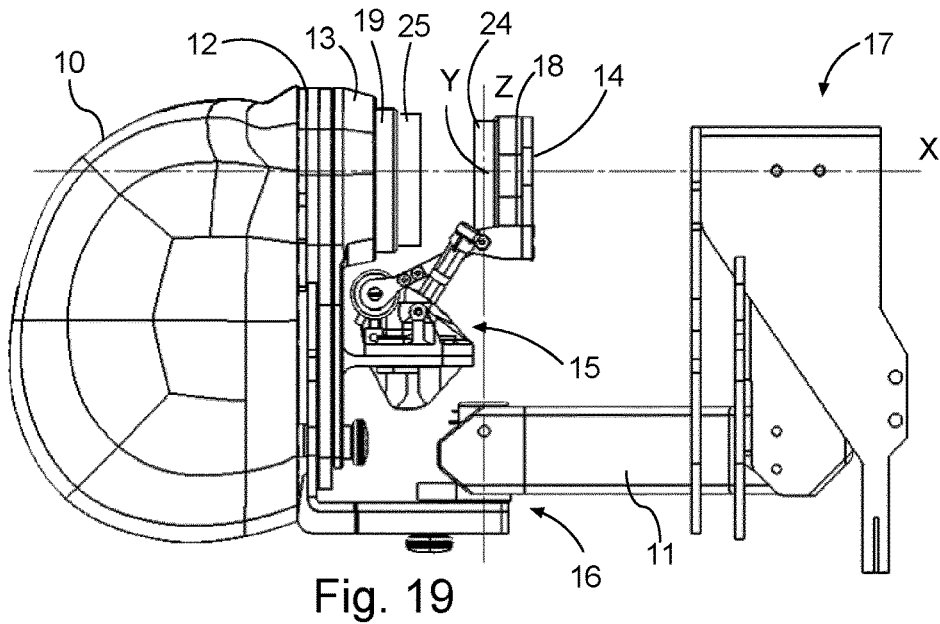
FIGS. 19 and 20 are side views of the phantom head of FIG. 12 illustrating different positions of the phantom lower jaw relative to the phantom upper jaw.
Figure 20:
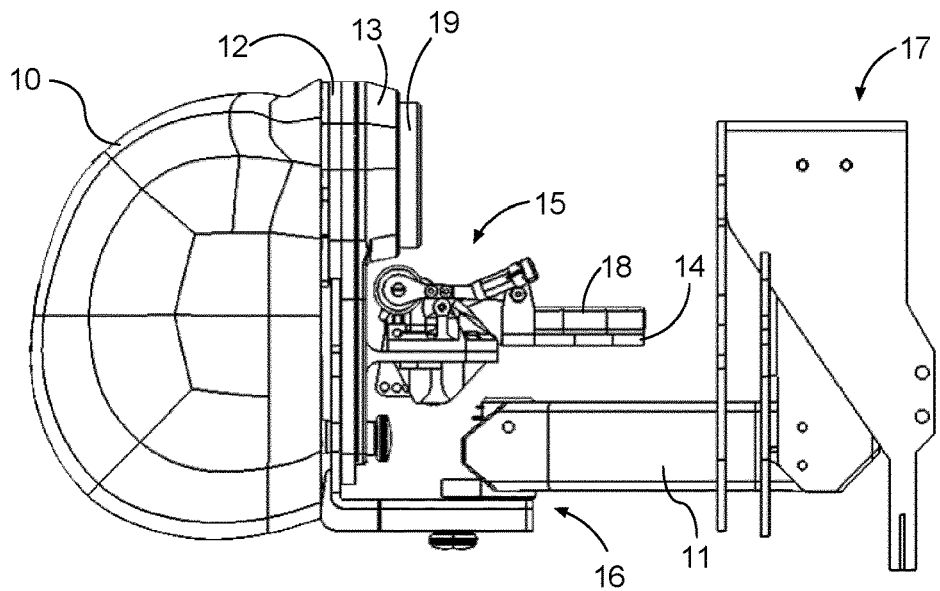
Figure 21:
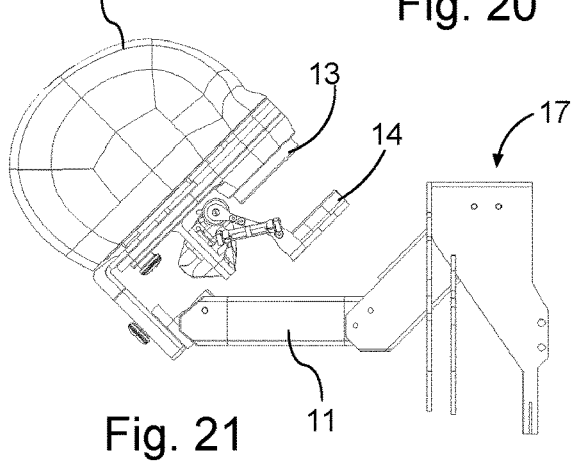
FIGS. 21 and 22 are side views of the phantom head of FIG. 16 illustrating rotation about the Y-axis.
Figure 22:
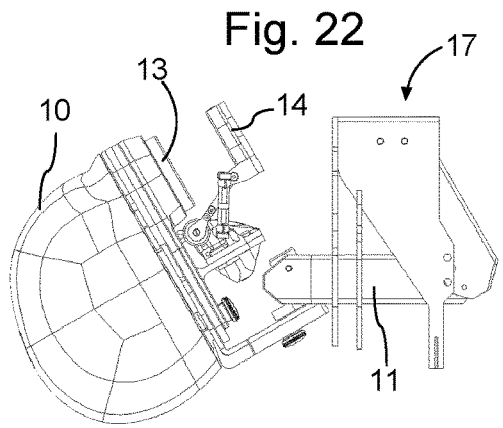
Figure 26:
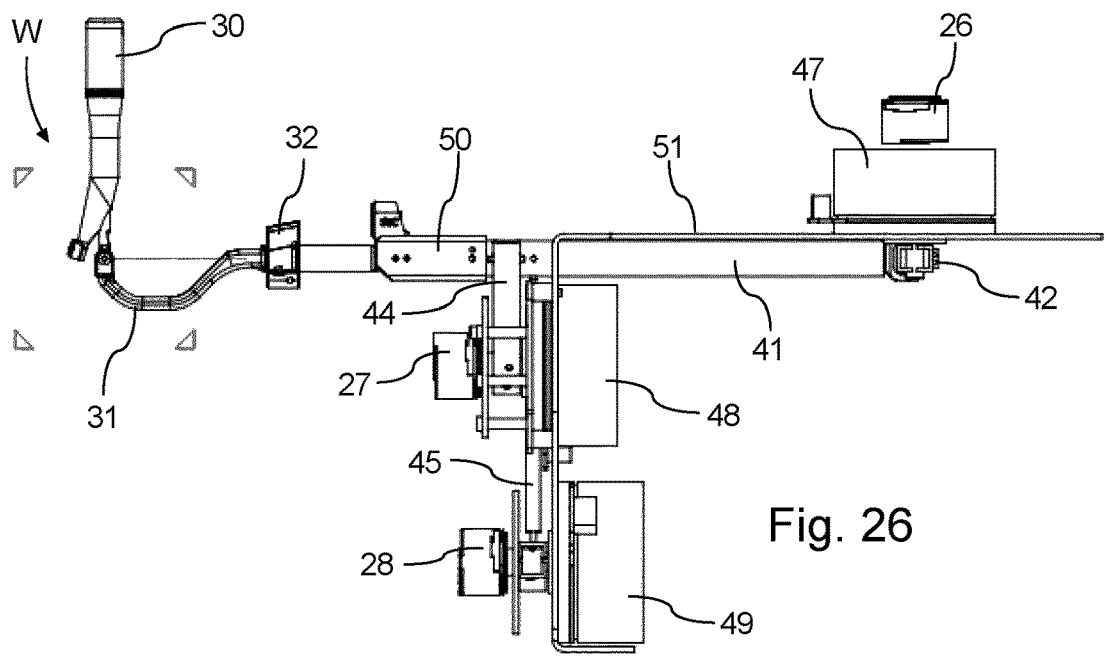
Figure 30:
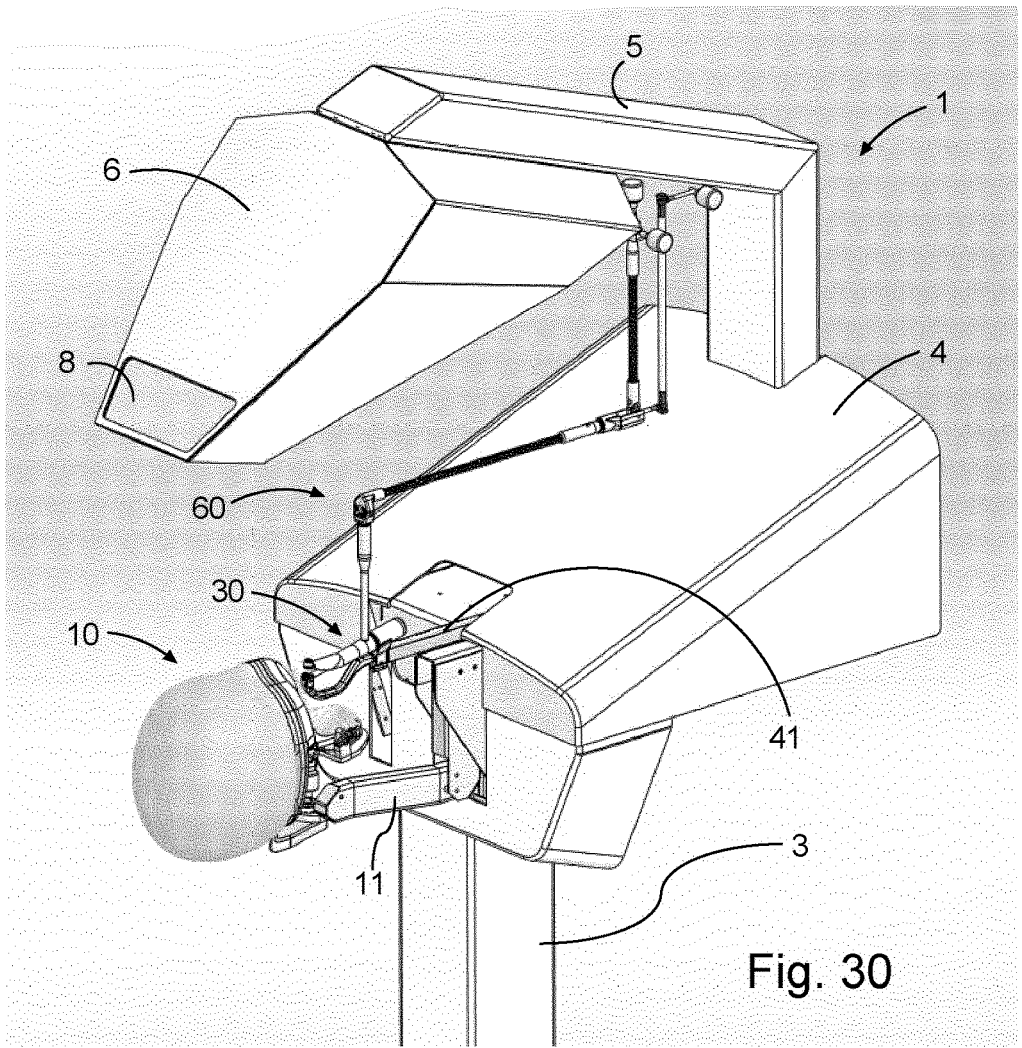
FIG. 30 is an elevated view of a dental procedure simulator according to another embodiment that comprises a secondary tool.

The phantom lower jaw 14 is suspended from the phantom upper jaw 13 to allow (manually imparted) movement between a fully open position and a closed position, as illustrated in FIGS. 19 and 20, respectively. A position sensor (not shown) is configured to create a signal indicative of the position of the phantom lower jaw 14 relative to the phantom upper jaw 13 and is connected to computer 80. The software is configured to adjust the position of a virtual lower jaw to the signal of the sensor.

The closed position of the phantom lower jaw 14 corresponds to a position for examining the occlusal reduction. The software is configured to display on a display screen 9 a set of virtual upper teeth for the virtual upper jaw and a set of lower virtual teeth for the virtual lower jaw, thereby allowing occlusal examination of the virtual set of teeth.

Figure 16:
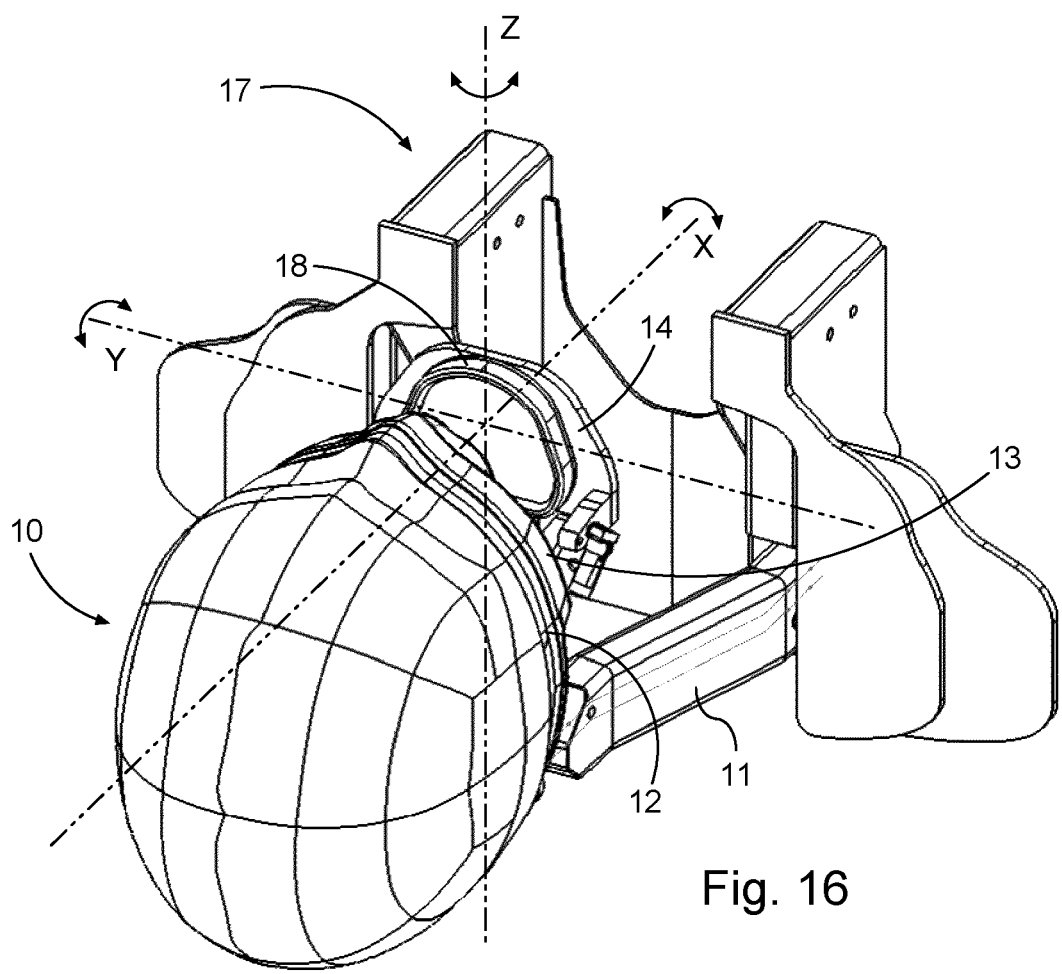
FIG. 16 is an elevated view of the phantom head of FIG. 12, illustrating three axes of rotation of the phantom head relative to the dental procedure simulator, with generic phantom jaws installed.
Figures 17, 18:
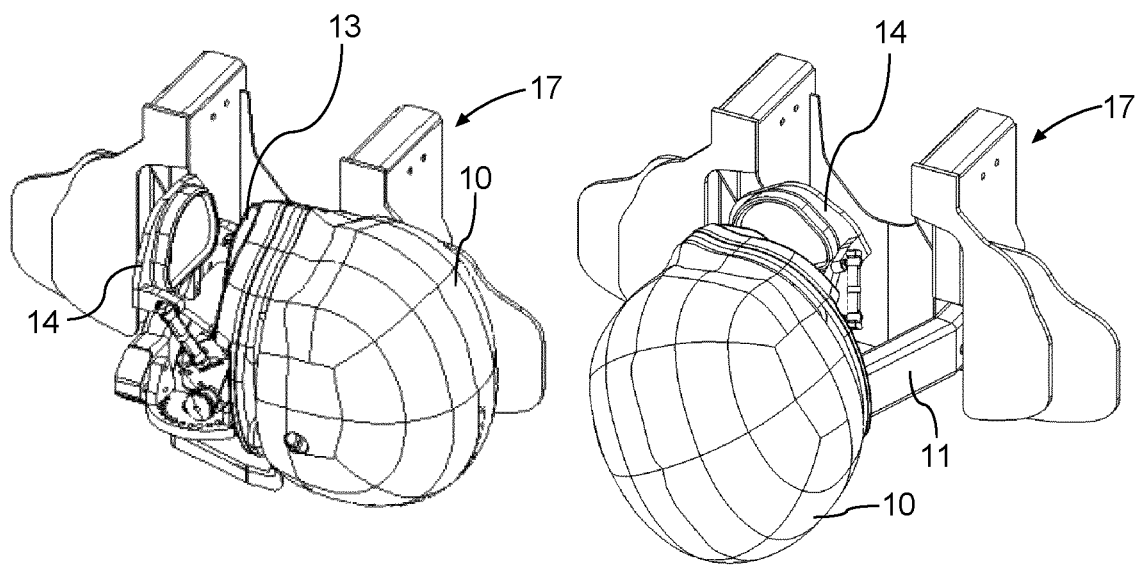
FIGS. 17 and 18 are elevated views of the phantom head of FIG. 16 illustrating rotation about the Z-axis and the X-axis.

The phantom upper jaw 13 is suspended from the support structure to allow rotation in three degrees of freedom, with the center of rotation for each degree of freedom being located between the phantom upper jaw 13 and the phantom lower jaw 14, i.e. in the center of the workspace W, so that the phantom upper jaw 13 does not leave the workspace W then it is rotated. The X,Y,Z axes of rotation are illustrated in FIG. 16. The rotation is manually imparted and preferably unison with the phantom head 10. Three rotary position sensors (not shown) for sensing rotation of the upper jaw 13 are provided for sensing rotation in each of the three degrees of freedom. The computer 80 is in receipt of a signal from the three rotary position sensors. The software is configured to adjust the simulation of the dental procedure or treatment to the signal from the rotary position sensors, in particular, the software adjusts the orientation and position of the virtual upper jaw and the orientation and position of the virtual lower jaw.

The phantom upper jaw 13 is suspended from the support structure by a first mechanism 11 that allows the upper jaw to rotate about a first horizontal axis Y that extends through the center of the workspace W without the first mechanism 11 intersecting the workspace W, the mechanism comprising a remote center linkage 11, preferably two spaced parallel remote center linkages 11 to render the mounting structure of the phantom head 10 more rigid and stable. The linkage 11 is connected to the main housing 4 by a bracket 17.

The phantom upper jaw 13 is suspended from the support structure by a second mechanism that allows the phantom upper jaw 13 to rotate about a second horizontal axis X that is disposed in the workspace W without the second mechanism intersecting the workspace W. The second mechanism comprises an L-shaped plate 12 that extends between the phantom head 10 and the phantom upper jaw 13. The phantom upper jaw 13 is connected through the L-shaped plate 12 by a hinge pin (not visible in the drawings) that allows the phantom upper jaw 13 and the phantom head 10 to rotate in unison about the second horizontal axis X.

The phantom upper jaw 13 is suspended from the support structure by a third mechanism 16 that allows rotation of the phantom upper jaw 13 about a vertical axis Z that extends through the center of the workspace W without the third mechanism 16 intersecting the workspace W. The third mechanism 16 comprises a hinge pin that connects the first mechanism 11 to the L-shaped plate 12 and allows the L-shaped plate 12 to rotate about the vertical Z-axis.

The phantom upper jaw 13 comprises an upper support member 19 with a removable phantom upper jaw element 21, 25 removably attached thereto, and the phantom lower jaw 14 comprises a lower support member 18 with a removable phantom lower jaw element 20, 24 removably attached thereto. In an embodiment, the removable phantom jaw elements 20, 21, 24, 25 are releasably attached to the upper or lower support element 18, 19 by magnetic force from the combination of a permanent magnet and a member of magnetic material, associated with the support element and phantom jaw element, respectively.

The generic phantom upper jaw element 25 and the generic phantom lower jaw element 24 do not have phantom teeth but are still considered to constitute a phantom upper jaw and phantom lower jaw, respectively. Thus, a phantom lower jaw or a phantom upper jaw can be formed by a simple U-shaped member that is substantially shaped and sized like a human lower jaw or upper jaw, preferably an average human lower jaw or upper jaw, though without teeth, and without recesses for receiving teeth. The generic phantom upper and lower jaws can be made from a polymer material, such as e.g. plastic, natural and/or synthetic rubber.

The specific phantom upper jaw element 20 and the specific lower jaw element 21 are provided with phantom teeth 22. The phantom teeth 22 are removably attached by the phantom teeth 22 being inserted in a specific recess 23 in the specific phantom upper or lower jaw element 20, 21. In an embodiment, the specific upper and lower jaw elements 20, 21 with their phantom teeth 22 are accurate models of a portion of a real human upper jaw and lower jaw with its upper teeth. The phantom tooth or teeth 22 that is/are to be subject to the dental procedure or treatment is/are removed to provide space for the first handpiece 30 to move unhindered by the phantom tooth or teeth 22 concerned. In FIGS. 8 to 11 one phantom tooth 22 has been removed by way of example and the recess 23 in the phantom jaw concerned 20, 21 is empty. The remaining phantom teeth 22 can be used by the user to support the user's hands and/or fingers. A virtual tooth will be displayed, linked, and co-located with the empty position/recess for the tooth concerned in the (upper or lower) phantom jaw, 13, 14 (or in specific lower jaw element 20/specific upper jaw element 21). Since the computer 80 is informed by sensors of the orientation and position of the respective upper and lower phantom jaws 13, 14, the computer 80 adapts the position and orientation of virtual teeth and in an embodiment also the position and orientation of the virtual jaws in the virtual model accordingly.

When a specific upper and/or lower phantom jaw element 20, 21 is used the computer 80 is provided with a virtual model of the specific lower jaw element 20 and/or of the specific upper jaw element 21. This virtual model can either include all of the teeth for the jaw concerned or only the virtual model of one or more teeth that correspond to the positions/recesses in the respective phantom jaw that is/are not provided with phantom teeth 22.

The computer 80 is configured to display on the display screen 9 a virtual environment comprising at least one virtual tooth co-located with the phantom upper jaw 13 or with the phantom lower jaw 14.

The phantom upper jaw 13 and the phantom lower jaw 14, 20 are movable relative to the support structure. The computer 80 is through one more sensors in receipt of the position and orientation of the phantom upper jaw 13, 21 and the phantom lower jaw 14, 20, and the computer 80 is configured to adjust the orientation and position of the at least one virtual tooth to movement of the phantom upper jaw 13, 21 or phantom lower jaw 14, 20 so that the at least one virtual tooth remains co-located on the display screen 9 with the phantom upper jaw 13, 21 or phantom lower jaw 14, 20 when the phantom upper jaw 13, 21 or phantom lower jaw 14, 20 is moved.

In an embodiment, the computer 80 is configured to display at least a portion of the virtual upper jaw and a portion of a virtual lower jaw 29, and the computer is configured to co-locate the virtual upper jaw with the phantom upper jaw 13 and to co-locate the virtual lower jaw 29 with the phantom lower jaw 14, on the display screen 9, also when the phantom upper jaw 13, 21 or the phantom lower jaw 14, 20 is moved relative to the support structure.

In an embodiment, the computer 80 is configured to co-locate the virtual tooth with said phantom upper jaw 13, 21, or with the phantom lower jaw 14, 20. Thus, regardless of the movement that the user may apply to the phantom jaws 13, 14, the computer will co-locate the virtual tooth with the phantom jaws 13, 14.

In an embodiment, the computer 80 is configured to display more than one virtual tooth and configured to co-locate the virtual teeth with the respective upper or lower phantom jaw 13, 14.

The computer 80 instructs the user which jaw element (generic or specific) is to be installed for a given exercise. Thus, the computer 80 is configured to instruct a user to install a generic upper or lower jaw element 25, 24 or a particular specific upper or lower jaw element 20, 21.

In the embodiment shown in FIGS. 12 to 21 the phantom upper jaw 13 and phantom lower jaw 14 are part of a phantom head 10. The phantom head 10 with its phantom lower jaw 14 and phantom upper jaw 13 is arranged movable relative to the support structure of the dental procedure simulator 1 and the phantom head 10 with its phantom lower jaw 14 and phantom upper jaw 13 to move in unison with one another.

Figure 37:
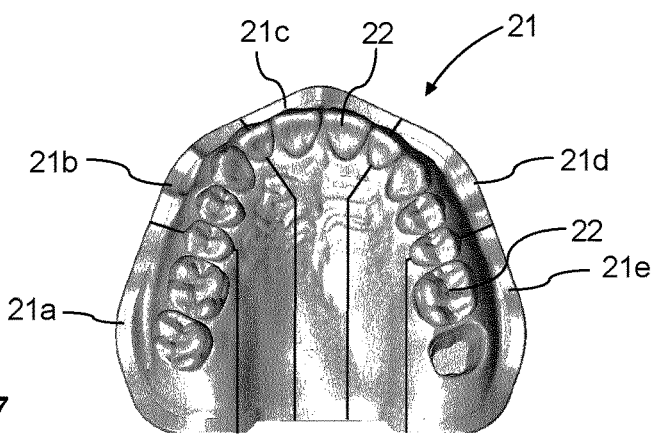
FIGS. 37 and 38 illustrate an embodiment of a segmented phantom jaw for use in a dental procedure simulator.
Figure 38:
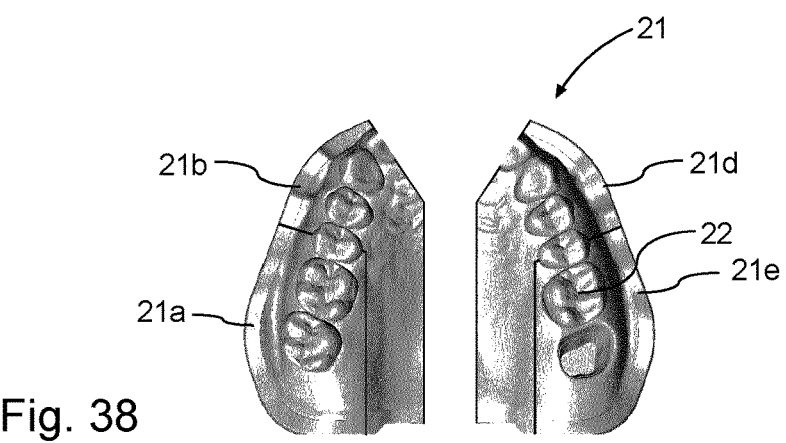

FIGS. 37 and 38 show an embodiment of a segmented upper jaw 22. In this embodiment, the phantom upper jaw 21 and/or the phantom lower jaw 20 is a segmented phantom jaw, in which at least one of the segments is removable. In the shown embodiment the segmented phantom jaw has five segments 21a, 21b, 21c, 21d, and 21e. Preferably, at least one of the segments is removable. FIG. 38 shows the phantom jaw with the center section 21c removed. In an embodiment, all of the seconds are removable, i.e. it can be taken out without using tools and reinstalled without the use of tools. The sections may slide into rails, attach magnetically, attached but with Velcro or other suitable releasable attachment means.

By using a segmented phantom jaw, in which at least one or more of the segments can be removed, it is possible to avoid abutment between the haptic arm and the phantom jaw, which can occur especially for activities that relate to simulated treatment of virtual teeth associated with the lower jaw. In other words, in some situations a portion of the phantom jaw is in the way for the haptic arm, in particular the handpiece link 31, and by removing the section 21a, 21b, 21c, 21d or 21e of the segmented phantom jaw concerned, place is made for the haptic arm, whilst most of the phantom jaw is still present for the user to use as support for their hands and for providing realism to the simulation.

Referring now particularly to FIGS. 23 to 26, which illustrate the linkage 40 that is controlled by the computer 80 to simulate the medical procedure or treatment. The linkage 40 comprises a main link 41 (in an embodiment an elongated straight member) and the first handpiece 30 is connected to a front extremity of the main link 41 by a mechanical joint with at least two degrees of freedom that will be explained in greater detail further below. The linkage 40 has a first crank 42 driven by a first rotary actuator 47, a second crank 44 driven by a second rotary actuator 48 and a third crank 46 driven by a third rotary actuator 49. The respective rotation axes of the first, second, and third cranks 42, 44, 46 can in an embodiment (not shown) be arranged orthogonally relative to one another.

The rotation axis of the first crank 42 extends substantially vertically. The first crank 42 is coupled directly (i.e. without an intermediate link in between) to the main link 41 at a first position which is at or near the rear extremity of the main link 41 by a hinge with two degrees of freedom, such as e.g. a universal joint.

The second crank 44 is directly (i.e. without an intermediate link in between) coupled to the main link 41 via a first horizontally extending connecting rod 43, preferably by a universal joint that allows rotation about two axes, and the third crank 46 is coupled to the main link 41 via a second vertically extending connecting rod 45. The first crank 42 is arranged to actuate the main link 41 in a first (horizontal) axial direction X. The second crank 44 is arranged to actuate the main link 41 in a second (horizontal) transverse direction Y, and the third crank 46 is arranged to actuate the main link 41 in a second (vertical) transverse direction Z.

The first connecting rod 43 is coupled to the main link 41 at a second axial position between the front extremity and the first position and the second connecting rod 45 is coupled to the main link 41 at a third axial position between the front extremity and the first position. In an embodiment, the second and third axial position substantially coincide.

The main link 41 comprises a three-dimensional force sensor (3DOF sensor) 50 for sensing forces applied by the user to the first handpiece 30 in three dimensions. The three-dimensional force sensor 50 is disposed between the front extreme position and the second and/or third axial position, and the three-dimensional force sensor 50 preferably is an integral part of the main link 41. The three-dimensional force sensor 50 is coupled (data connection) to the computer 80, e.g. by signal cables.

The first, second, and third cranks 42, 44, 46 are coupled (directly or to the rotary motor driving the respective crank) to respective first second and third rotary position sensors or encoders 26, 27, 28, which are in data connection with the computer 80. In the shown embodiment, the rotation axis of the second crank 44 and of the third crank 46 both extend horizontally and parallel. However, the rotation axis of the second crank 44 and of the third crank 46 main embodiment also extends horizontally and at an angle to one another, for example, a right angle.

The first, second, and third cranks 42, 44, 46 are mounted on a reference 51 (e.g. a frame or base). The reference 51 is supported by the main housing 4 or by the support structure of the dental procedure simulator 1. The linkage 40 connects the handpiece 30 to the reference 51 and the linkage 40 provides six independent degrees of freedom for the handpiece 30 relative to the reference 51.

A handpiece rest 32 provides a parking position for the first handpiece 30 when the first handpiece 30 is not used. A park sensor 59 is associated with the handpiece rest 32 to detect the parked position of the first handpiece 30.

The arrangement of the linkage 40 results in a workspace W in which the first handpiece 30 can be manipulated by a user that is shaped as a cuboid with a horizontal top and bottom.

Figure 27:
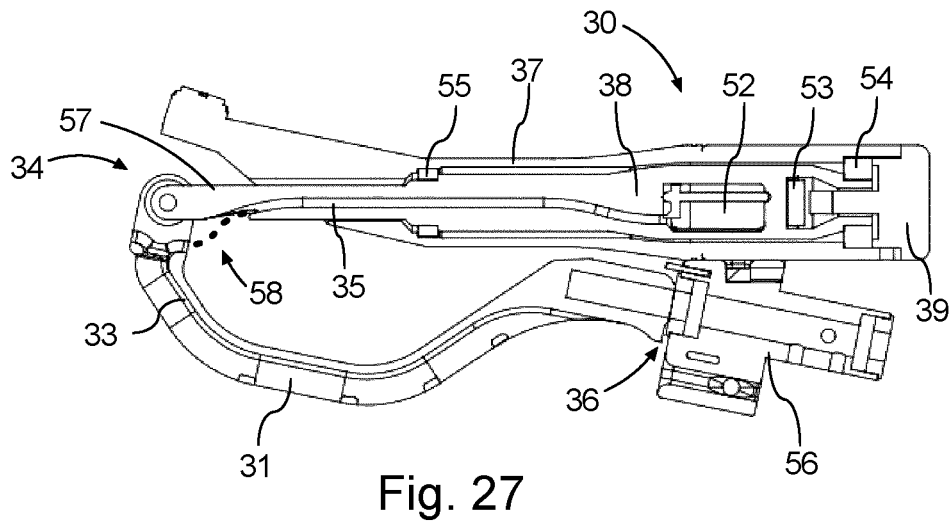
FIG. 27 is a sectional view through a handpiece according to an embodiment.
Figure 28:
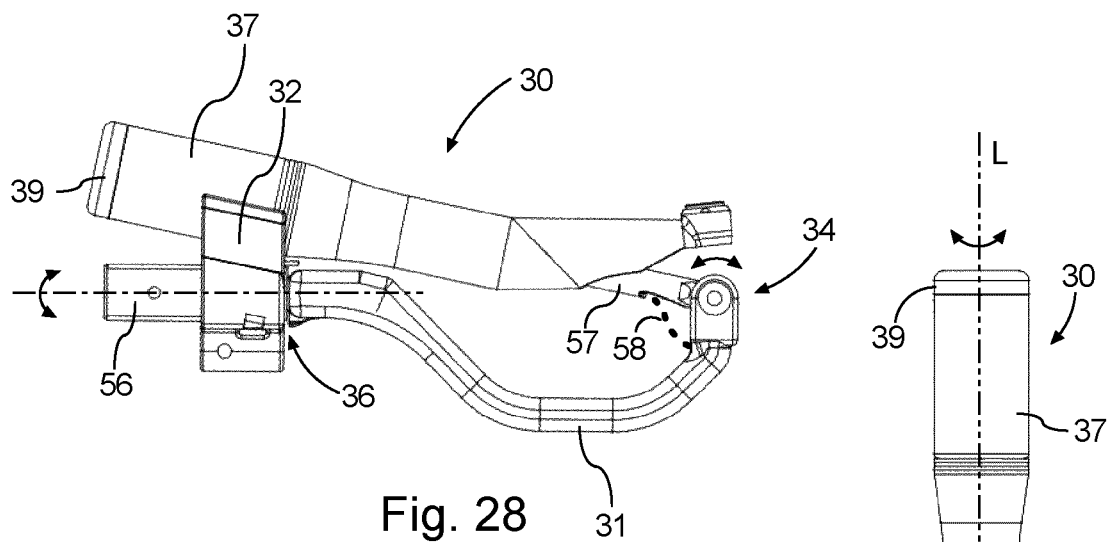
FIGS. 28 and 29 are side views of the handpiece of FIG. 27.
Figure 29:
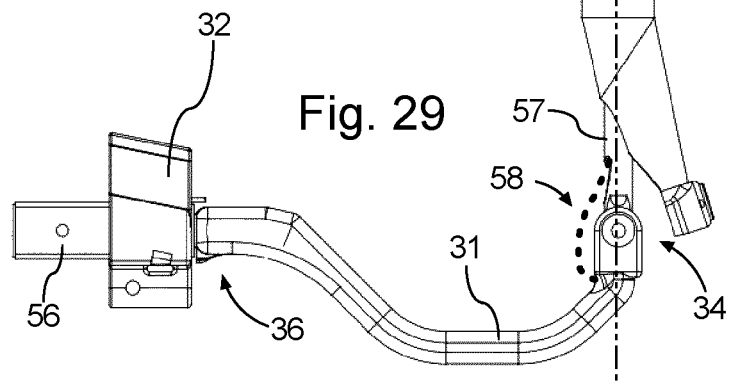
Figure 31:
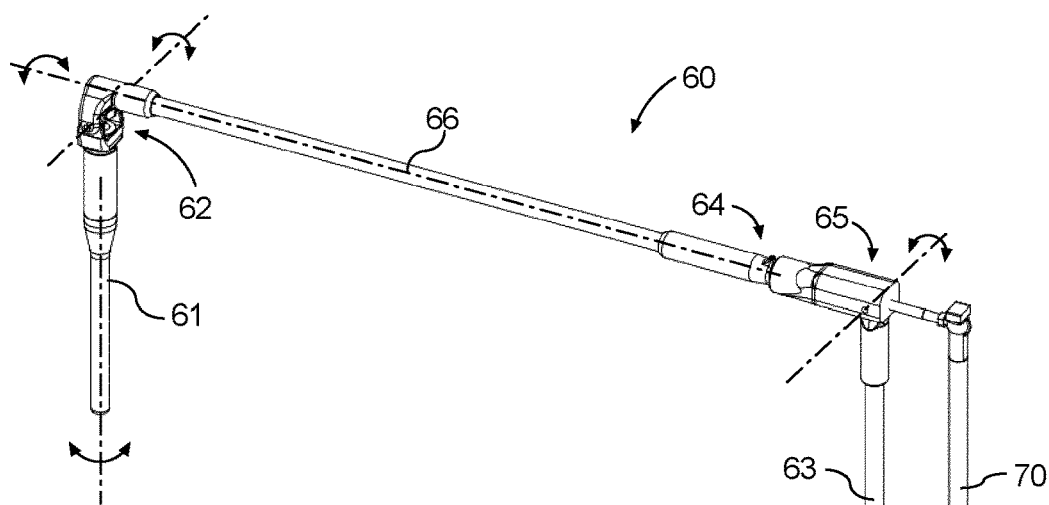
FIG. 31 is an elevated view of an embodiment of the secondary tool.
Figure 33:
FIGS. 32 and 33 are end and side views, respectively of the secondary tool of FIG. 31.
Figure 33:
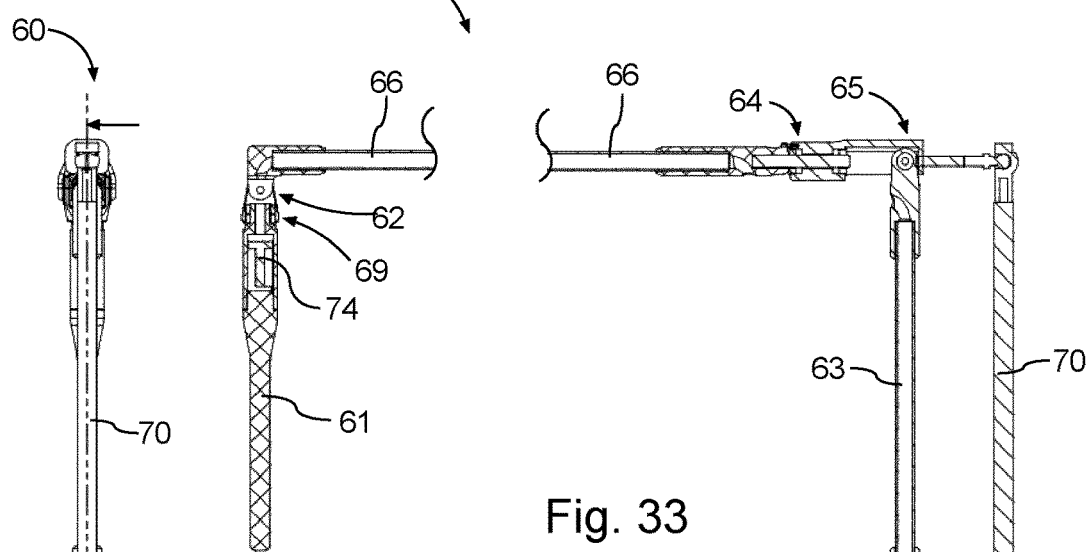
Figure 32:
Figure 34:
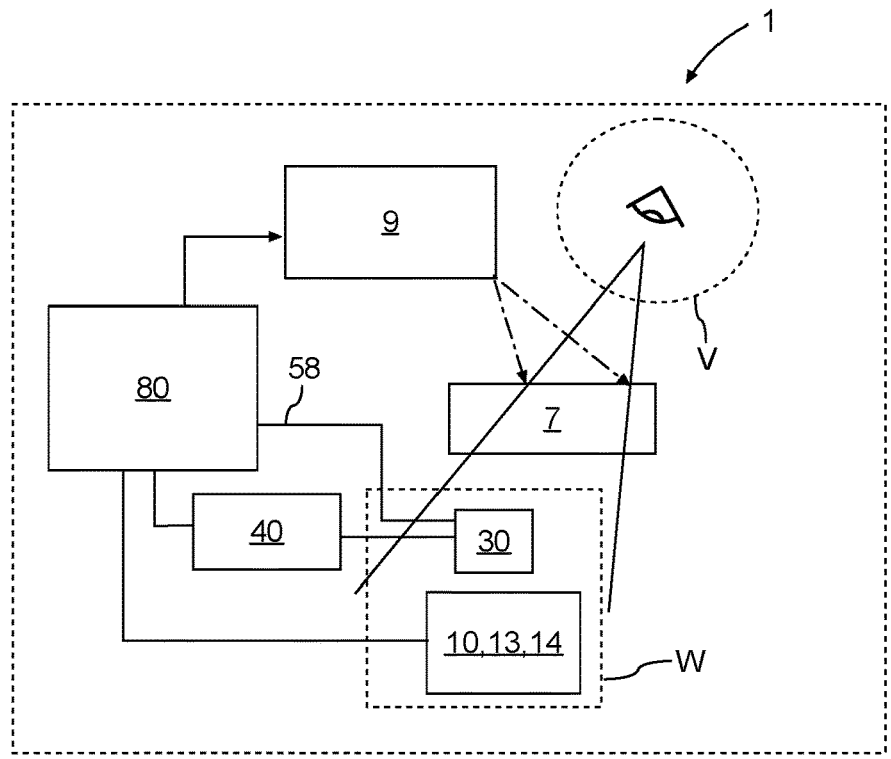
FIG. 34 is a schematic representation of the dental procedure simulator of FIG. 1 showing also an eye of a user and a vision space.

Referring now particularly to FIGS. 27 to 29, which illustrate the first handpiece 30 in greater detail. The first handpiece 30 comprises an inner part 38 extending into an outer part 37 with the outer part 37 being configured to rotate about the inner part 38. The outer part 37 forms the outer shell of the first handpiece 30 and is configured to rotate about the inner part 38 about a longitudinal axis L of the handpiece 30. A portion 57 of the inner part 38 protrudes from the outer part 37 and the portion 57 is coupled to the front extremity of the linkage 40 by a joint with at least two degrees of freedom. This joint comprises a handpiece link 31 coupled at one of its extremities to the inner part 38 by a first pivot hinge 34 to provide one degree of freedom. The other extremity of the handpiece link 31 is attached to a connection element 56 by a first pivot joint 36 to provide a second degree of freedom. The connection element 56 is rigidly connected to the extremity of the main link 41.

A first inertial measurement unit 52 is mounted to the inner part 38. A fourth rotary position sensor 53 senses rotational movement of the outer part 37 relative to the inner part 38. The fourth rotary position sensor 53 is mounted on the inner part 38 and arranged to measure the rotational position of the outer part 37 relative to the inner part 38. At least a first portion of the fourth rotary position sensor 53 is mounted on the inner part 38, and the first portion is connected to the computer 80 by a cable 58 that is guided or supported by the inner part 38.

The first inertial measurement unit 52 and the fourth rotary position sensor 53 are coupled to the computer 80 by a cable 58 that is received in a cable channel 35 that extends through the inner part 38. The cable 58 leaves the inner part 38 near the first hinge 34 and then enters a cable channel 33 that extends through the handpiece link 31. The cable 58 establishes a data link between the inertial measurement unit 52 and the computer 80 for transmission of position and/or orientation data and between the fourth rotary position sensor 54 and the computer 80 for transmission of rotational position data.

A cap 39 forms the free end of the first handpiece 30. A first rotary bearing 54 and an axially spaced second rotary bearing 55 are arranged between the inner part 38 and the outer part 37. Due to the absence of limiting structures the outer part 37 has infinite roll relative to the inner part 38.

The inner part 38 is elongated and is connected to the handpiece link 31 at a first extremity of the inner part 38. The fourth rotary position sensor 53 is arranged at or near a second extremity of the inner part 38, the second extremity being located inside the outer part 37.

The longitudinal extent of the outer part 37 comprises a proximate portion (proximate to the user) and a distal portion (distal to the user). The distal portion extends at an angle to the proximate portion, with the inner part 38 protruding from the outer part 37 through the distal portion.

The first inertial measurement unit 52 is positioned within the outer shell 37 of the handpiece 30 and mounted on the inner part 38. The first inertial measurement unit 52 is configured to measure translational acceleration, rotational velocities, and the magnetic field. As such, the first inertial measurement unit 52 is also capable of determining the speed and displacement of the first handpiece 30 using data processing techniques known in the art. In an embodiment, the first inertial measurement unit 52 has nine sensors, which comprise a 3-axis gyroscope, a 3-axis accelerometer, and a 3-axis magnetometer. The first inertial measurement unit 52 is provided with an embedded Digital Motion Processor that acquires data from accelerometers, gyroscopes, magnetometers and processes the data. The inertial measurement unit chip outputs a quaternion, which describes the orientation in space to a reference, e.g. in real space. This data output is passed along the cable 58 along with the signal from the fourth rotary position sensor 53 to the computer 80.

The inertial measurement unit 52 is calibrated before use by placing the handpiece 30 with a defined orientation so that world reference is in alignment. This embodiment uses the park position on the handpiece rest 32 shown in FIG. 28 for the calibration.

Referring now particularly to FIGS. 30 to 33, which illustrate another embodiment of the dental procedure simulator 1. In this embodiment, structures and features that are the same or similar to corresponding structures and features previously described or shown herein are denoted by the same reference numeral as previously used for simplicity.

In this embodiment a secondary tool 60 with a second handpiece 61 is added, e.g. to simulate a mirror tool used by a dentist. Unlike the first handpiece 30, whose real world position is controlled by the dental procedure simulator 1, the real world position of a second handpiece 61 is controlled by the user (the secondary tool 60 is not actuated and is moved manually without haptic feedback). The secondary tool 60 is suspended from the support arm 5 and comprises a second handpiece 61 that can be manipulated in the workspace W by a user. The secondary tool 60 is suspended from the main structure of the dental procedure simulator by a linkage. The computer 80 is configured to display a corresponding virtual secondary tool in the virtual environment e.g. a virtual dental mirror corresponding to real world dental mirror handle. The position and movement of the virtual second handpiece is adjusted to directly match the real world position of second handpiece 61.

The secondary tool 60 comprises a primary link 63 coupled to the structure of the dental procedure simulator 1 by one or more joints that provide a first and second degree of freedom and a secondary link 66 coupled to the primary link 63 by one or more joints that provide a third and fourth degree of freedom. The second handpiece 61 is connected to the secondary link 66 by one or more joints that provide a fifth and sixth degree of freedom to form a serial chain that connects the handpiece 61 to the main structure of the dental procedure simulator 1 with six degrees of freedom. A fifth rotary position sensor 68 senses movement in the first degree of freedom, a sixth rotary position sensor 72 for sensing movement in the second degree of freedom, and a seventh rotary position sensor 73 for sensing movement in the third degree of freedom. The fifth, sixth and seventh position sensors 68,72,73 being in data connection with the computer 80, A second inertial measurement unit 74 is arranged in the second handpiece 61 and moves in unison with the second handpiece 61. The second inertial measurement unit 74 is in data connection with the computer 80 and the second inertial measurement unit 74 is configured to sense movements in at least the fourth, fifth, and sixth degrees of freedom. The second inertial measurement unit 74 is in an embodiment technically identical to the first inertial measurement unit 52.

The second handpiece 61 is connected to the secondary link 66 by a fourth pivot joint 69 that provides the sixth degree of freedom. The sixth degree of freedom allows the second handpiece 61 rotate about an (longitudinal) axis of the second handpiece 61. The second inertial measurement unit 74 is configured to sense the sixth degree of freedom.

The fourth pivot joint 69 is connected to an extremity of the secondary link by a second hinge 62 that provides the fifth degree of freedom of the second handpiece 61.

The second handpiece 61 can move in three translational degrees of freedom and the second handpiece 61 itself can move in three rotational degrees of freedom.

The primary link 63 is an elongated link such as e.g. a rod or a tube. The primary link 63 is coupled to the reference (e.g. the support structure of the dental procedure simulator 1) by a fourth hinge 75 that allows the primary link 63 to rotate about a transverse axis (transverse to the longitudinal extent of the primary link 63) to obtain the second degree of freedom.

The primary link 63 is coupled to the fourth hinge 75 by a third pivot joint 67 that allows the primary link 63 to rotate about its longitudinal axis to realize the first degree of freedom.

The fifth rotary position sensor 68 is arranged to sense rotation about the longitudinal axis of the primary link 63 and the second rotary position sensor 72 is arranged to sense rotation about the third hinge 75.

The secondary link 66 is an elongated link that is coupled to the primary link 63 by a third hinge 65 that allows the secondary link 66 to rotate about a transverse axis (transverse to the longitudinal axis of the secondary link 66) to obtain the third degree of freedom.

The seventh rotary position sensor 73 is configured to sense rotational movement of the secondary link 66 about the third hinge 65. The secondary link 66 is coupled to the third hinge 65 by a second pivot joint 64 that allows the secondary link 66 to rotate about its longitudinal axis to obtain the fourth degree of freedom.

A tertiary link 70 is coupled to a quaternary link 71. The tertiary link 70 is coupled to the primary link 63 or to the secondary link 66, and the quaternary link 71 is coupled to the seventh rotary position sensor 73 to form a serial chain that translates rotation of the secondary link 66 about the transverse axis of the secondary link 66 (about the third hinge 65) into rotational movement of the seventh rotary position sensor 73.

The second inertial measurement unit 74 is configured to sense rotation of the handpiece 61 about the (longitudinal) axis of the handpiece 61, i.e. to sense the movement in the sixth degree of freedom. The second inertial measurement unit 74 is in data communication with the computer 80, preferably by a wireless (RF) data connection.

In an embodiment (not shown) a rotary position sensor is arranged inside the second handpiece 61 for sensing rotation of the handpiece 61 about the longitudinal axis of the handpiece 61.

In an embodiment, the second inertial measurement unit 74 is configured to sense movement in all six degrees of freedom and the computer 80 is configured to use the signal from the fifth, sixth and/or seventh sensors 68, 72, 73 as a reference for calibrating the inertial second measurement unit 74.

Generally, the computer 80 is configured to both receive information indicating the rotational position of first second and third cranks, and to control actuation of the first second and third cranks (global linear movement of the first handpiece 30, to receive information indicative of actuation of the first handpiece 30 and the second handpiece 61, and, to receive information indicative of the orientation (rotational position) of the first handpiece 30 from the first inertial measurement unit 52 and information indicative of the orientation (rotational position) of the second handpiece 61 from the second inertial measurement unit 74. A control scheme is used in which the position, orientation, and actuation of the first handpiece 30 is known by the computer 80, which is also able to provide haptic feedback to the first handpiece 30 via the actuators 47, 48, 49 as determined by the characteristics of the virtual model. The position of the virtual tools within the virtual environment is displayed on the display screen 9.

By using data from the rotary position sensors 26, 27, 28, 68, 72, 73 associated with first linkage 40 and the secondary linkage 60 and from the first and second inertial measurement units 52, 74, as well as the rotary position sensor 53, the position and orientation of the virtual tools within the virtual environment is displayed on the display screen 9 so as to be co-located with the position and orientation of the real tools.

In an embodiment, the computer 80 is configured to simulate a medical procedure or treatment through haptic feedback, preferably haptic force feedback, with the linkage 40 with its associated actuators 47, 48, 49, and through visual feedback with the display screen 9. Hereto, the computer 80 is configured to use the signal from the three-dimensional force sensor 50 as input and by controlling the position of the extremity of the linkage 40 accordingly.

In an embodiment, the computer 80 includes software applications for providing a training platform, providing instructional material and videos, recording, replaying and evaluating a user's performance; providing audio, visual and textual communication with a remote instructor over a computer network; providing a remote instructor ability to provide force inputs to the haptic system; and providing differing virtual objects (e.g. teeth, jaws or complete heads), tools and physical rules into the virtual environment.

In an embodiment, the computer 80 is configured to detect collision between a burr of a virtual dental drill (using the real position of the first tool 30), to determine the interaction force to be applied to the virtual drill based upon virtual drill position, a virtual drill model and a virtual tooth model. The computer 80 is also configured to calculate the virtual drill speed based upon the interaction force and a user input, such as from a foot pedal.

In an embodiment, the tooth model volume is represented as a set of three-dimensional pixels or voxels. Each voxel has a hardness value associated with it, representing the type/quality of tooth material (i.e. dentin, enamel, pulp). The conventional marching cubes algorithm is used to create a triangle mesh of an isosurface of the tooth model voxel set.

The virtual handpiece is modeled analytically or by voxels. Thus, the handpiece's physical model a finite number of voxels, or by a complete analytically defined shape. The handpiece model also has a vector parameter for the handpiece's three-dimensional velocity. The virtual tool is provided with a virtual burr. The virtual burr or virtual handpiece can come in virtual contact with the virtual tooth. Hereto, the shape of the virtual burr is rendered against the voxels of the virtual tooth. The real position of the first handpiece 30 is used to determine the position of the virtual burr and to determine contact between the virtual burr and the virtual tooth.

Figure 35:
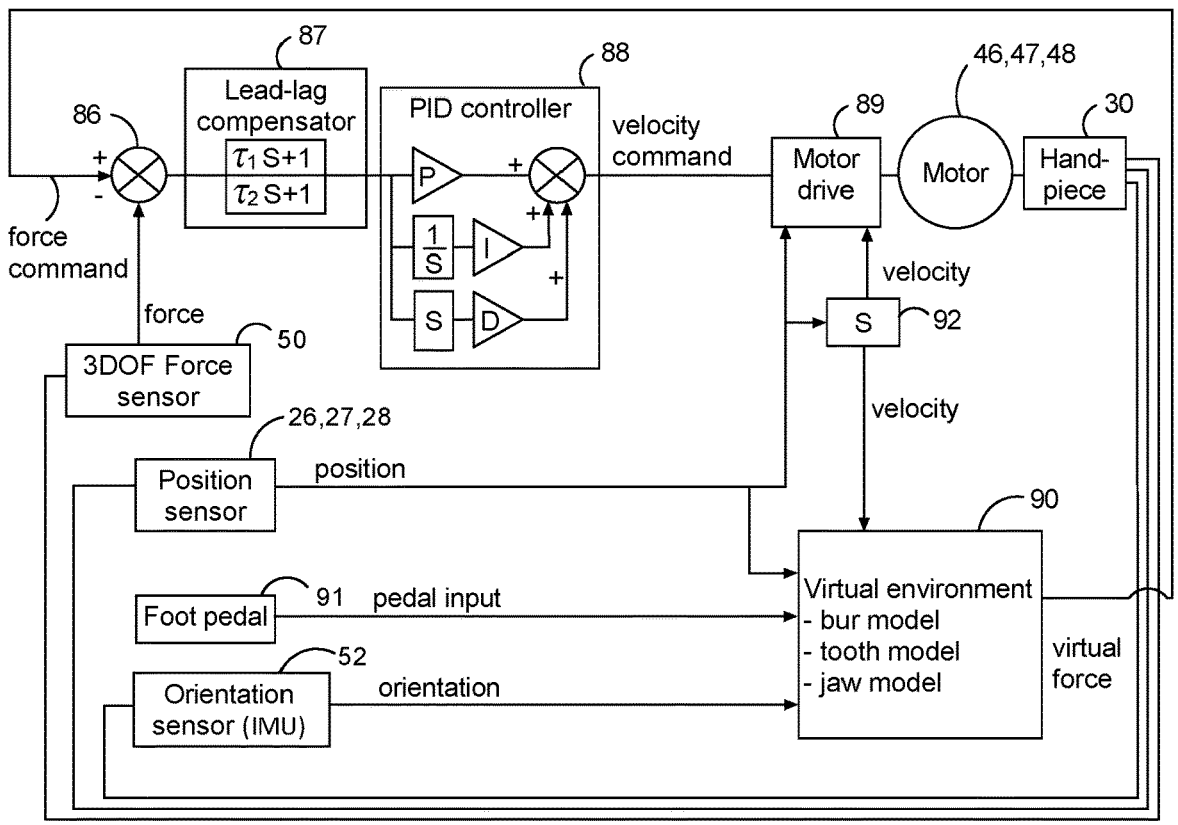
FIG. 35 is a schematic representation of an embodiment of a control system that can be used in the dental procedure simulator.

Referring now in particular to FIG. 35 a control loop is used to control the velocity in one direction of the end of the main link 41 and thereby the velocity of the first handpiece 30. In total 3 of these force control loops are active to control the 3 directions of movement (3DOF). The force control loop uses the difference between the virtual force that is calculated by virtual environment 90 and the real force in one direction that is calculated from the force measured by the 3DOF force sensor 50 at a summation point 86. The output of the summation point 86 is the input for a lead-lag compensator 87 that removes high frequencies and connects into a standard PI or PID controller 88. The PI or PID controller calculates a velocity command for the motor drive 89. The motor drive 89 is also in receipt of a signal from the rotary position sensors (encoders) 26, 27, 28 and determines the actual velocity of the handpiece 30 from the position signal. The motor drive 89 electrically drives the first rotary actuator 47, (the motor drives of the other two control loops drive the second rotary actuator 48 and the third rotary actuator 49). The motor drive uses the difference between the velocity command of the PI or PID controller and the real velocity that is calculated from the real position that is measured by the position sensor (encoder) 26, 27, 28 on the respective rotary actuator 46, 47, 48. A differentiator 92, receives the position signal provides the actual velocity as an output signal. The output of the differentiator 92 is provided to the motor drive 89 and to the virtual environment 90. In an embodiment, the differentiator 92 is an integral part of the motor drive 89. The first second and third rotary actuators 47, 48, 49 are connected to the first handpiece 30 via the linkage 40 that connects to the different sensors (force, position, and orientation) described above. Input from a foot pedal sensor 91 (connected to the dental procedure simulator 1 and to the computer 80 via a data cable) is used to determine the rotary speed of the virtual burr. The virtual environment receives a signal from IMU 52 to be informed of the orientation of the first handpiece 30. The virtual environment 90 includes a burr model, a tooth model, and a jaw model and uses the real position and the real orientation of the first handpiece 30 to determine the position and orientation of the virtual burr. The virtual burr model and the virtual tooth model or jaw model are used to calculate the resulting virtual force that is sent back as a command to the force control loop and applied to the handpiece 30.

When beginning with the dental procedure simulator 1, the user positions herself in a chair (not shown) in front of the dental procedure simulator 1. If the display screen 9 is an autostereoscopic display screen the user does not need to use shutter glasses or glasses with polarized lenses. The height of the main housing 4 is properly adjusted to the ideal working height for the user concerned. The chair height can also be adjusted according to the need of the user concerned.

The dental procedure simulator is in an embodiment provided with a network (e.g. LAN, WAN) connection through the computer 80.

Figure 36:
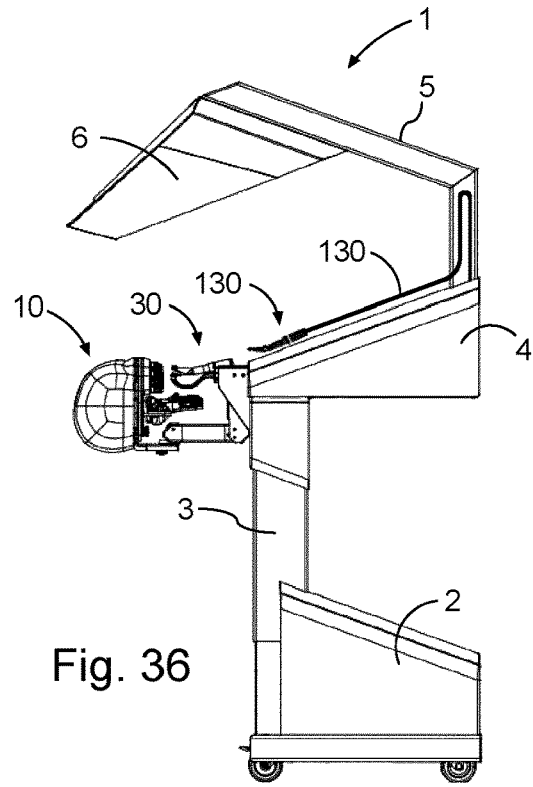
FIG. 36 shows another embodiment of the dental procedure simulator with an additional function of training drilling into plastic phantom teeth.

FIG. 36 shows another embodiment, in which the functionality of the dental procedure 1 simulator is enhanced by adding the possibility to train the user by drilling into plastic teeth with a conventional dental handpiece 130 that includes a motor-driven drill. In this embodiment at least the upper or lower phantom jaw is provided with one or more phantom teeth 22 of a polymer (plastic) material that is suited for being drilled in with a dental drill. The phantom teeth 22 are removably attached by the phantom teeth 22 being inserted in a specific recess 23 in the specific phantom upper or lower jaw element 20, 21. Thus, the polymer material teeth 22 can be replaced after they have been drilled into, or they can be replaced in order to provide another exercise with a different tooth 22. In this embodiment, the specific upper and lower jaw elements 20, 21 with their phantom teeth 22 are preferably accurate models of a portion of a real human upper jaw and lower jaw with its upper teeth, made from a suitable polymer (plastic) material. The phantom tooth or teeth 22 that is/are is to be subject to the dental procedure or treatment for training the (aspiring) dentist are drilled in by using the conventional dental handpiece 130. The conventional dental handpiece 130 is powered (electrically or pneumatically) through a cable 133 that connects the conventional dental handpiece 130 to the main housing 4 for powering a pneumatic or electric motor in the conventional dental handpiece 130. The pneumatic or electric motor drives a dental burr (not shown), that is used to drill into the plastic teeth 22. The cable 133 also provides pressurized water to the conventional dental handpiece 130 for spraying water onto the workspace.

In a variation of this embodiment, the apparatus 1 is configured to operate in another mode when the user uses the conventional dental handpiece 130 drilling into plastic teeth. Accordingly, the computer 80 runs a specific training program suitable for training by drilling with a conventional dental handpiece 130 into plastic teeth 22.

The computer 80 can be programmed to enhance the user experience when drilling with a conventional dental handpiece 130 into plastic teeth 22 by graphics on the display screen 9 and/or by audio information through a loudspeaker. Thus, the training experience can be enhanced by providing instructions or feedback on user performance on the display screen 9 or via a loudspeaker.

The computer 80 has at least a first mode of operation for simulating a dental procedure or treatment using the handpiece 30 and a second mode of operation for training a dental procedure or treatment using the conventional powered dental handpiece 130.

In this disclosure, any reference to a body part, such as e.g. teeth, lower jaw, upper jaw, or head, typically referred to the human versions of these body parts. Thus, in this disclosure e.g. phantom lower jaw is a physical model of a human lower jaw and e.g. a virtual lower jaw is a virtual model of the human lower jaw. The resemblance of the phantom body parts to real body parts is preferably at a level that at least the shape of the phantom part closely resembles the shape of the real body part to an extent that the phantom body part provides a realistic impression of the body part concerned to the user.

The various aspects and implementations have been described in conjunction with various embodiments herein. However, other variations to the disclosed embodiments can be understood and effected by those skilled in the art in practicing the claimed subject-matter, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems.

The reference numerals used in the claims shall not be construed as limiting the scope. Unless otherwise indicated, the drawings are intended to be read (e.g., cross-hatching, arrangement of parts, proportion, degree, etc.) together with the specification, and are to be considered a portion of the entire written description of this disclosure. As used in the description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

The invention claimed is:

1. A dental procedure simulator comprising:
a support structure,
a display screen,
a computer configured to simulate a dental procedure or treatment,
a linkage suspended from said support structure, said linkage being controlled by said computer to simulate a medical procedure or treatment by providing haptic force feedback,
a handpiece operably coupled to said linkage and configured to be held in a hand of a user and to be manipulated by the user in a predefined workspace (W) of the dental procedure simulator in real space,
a phantom upper jaw and a phantom lower jaw movably supported by said support structure and arranged in said workspace (W),
wherein said phantom upper jaw is movable relative to said support structure,
said dental procedure simulator comprises rotary position sensors configured to sense the position and orientation of said phantom upper jaw and said phantom lower jaw relative to said support structure,
said computer being configured to display on said display screen a virtual environment comprising at least one virtual tooth co-located with said phantom upper jaw or with said phantom lower jaw.

2. The dental procedure simulator according to claim 1, wherein said computer is configured to create a virtual environment comprising a virtual handpiece, a virtual upper jaw, and a virtual lower jaw, said computer being configured to display said virtual environment on said display screen, and said computer being configured to:
co-locate said virtual handpiece with said handpiece,
one or more of co-locate said virtual upper jaw with said phantom upper jaw, and co-locate said virtual lower jaw with said phantom lower jaw.

3. The dental procedure simulator according to claim 1, wherein said phantom lower jaw is arranged movably relative to said phantom upper jaw.

4. The dental procedure simulator according to claim 1, wherein said phantom upper jaw and said phantom lower jaw are provided with one or more recesses for receiving a phantom tooth, and wherein said at least one virtual tooth is co-located on said display screen with one of said one or more recesses for receiving a phantom tooth.

5. The dental procedure simulator according to claim 1, wherein said phantom upper jaw is movable relative to said support structure,
wherein said computer is through said rotary position sensors in receipt of the position and orientation of said phantom upper jaw and said phantom lower jaw, and said computer being configured to adjust the orientation and position of said at least one virtual tooth to movement of said phantom upper jaw and of said phantom lower jaw so that said at least one virtual tooth remains co-located on said display screen with said phantom upper jaw or phantom lower jaw when said phantom upper jaw or phantom lower jaw is moved.

6. The dental procedure simulator according to claim 1, wherein said computer is configured to display at least a portion of said virtual upper jaw and a portion of said virtual lower jaw, the computer being configured to co-locate said virtual upper jaw with said phantom upper jaw and to co-locate said virtual lower jaw with said phantom lower jaw on said display screen, also when said phantom upper jaw or said phantom lower jaw is moved.

7. The dental procedure simulator according to claim 1, wherein said phantom lower jaw is suspended from said phantom upper jaw by a hinge mechanism that comprises a four-bar linkage that imitates the movement of a human jaw.

8. The dental procedure simulator according to claim 1, wherein said phantom lower jaw is suspended from said phantom upper jaw to allow movement between an open position and a closed position.

9. The dental procedure simulator according to claim 8, wherein said closed position corresponds to a position for examining the occlusal reduction and wherein said computer is configured to display on a display screen a set of virtual upper teeth for said phantom upper jaw and a set of lower virtual teeth for said phantom lower jaw, thereby allowing visual occlusal examination of the virtual set of teeth in said closed position.

10. The dental procedure simulator according to claim 8, wherein the rotary position sensors are configured for sensing rotation of said phantom upper jaw for each of said one to three degrees of freedom.

11. The dental procedure simulator according to claim 1, wherein the rotary position sensors comprise a position sensor configured to create a signal indicative of the position of said phantom lower jaw relative to said phantom upper jaw.

12. The dental procedure simulator according to claim 1, wherein said phantom upper jaw is suspended from said support structure to allow, rotation in one, two, or three rotational degrees of freedom with the center of rotation for each degree of freedom being located between said phantom upper jaw and said phantom lower jaw.

13. The dental procedure simulator according to claim 1, wherein said phantom upper jaw is suspended from said support structure by a first mechanism that allows said upper jaw to rotate about a first horizontal axis Y that is disposed in said workspace (W) without said first mechanism intruding said workspace (W).

14. The dental procedure simulator according to claim 1, wherein said phantom upper jaw is suspended from said support structure by a second mechanism that allows said phantom upper jaw to rotate about a second horizontal axis X that is disposed in said workspace (W) without said second mechanism intersecting said workspace (W).

15. The dental procedure simulator according to claim 1, wherein said phantom upper jaw is suspended from said support structure by a third mechanism that allows rotation of said phantom upper jaw about a vertical axis Z, without said third mechanism intersecting said workspace (W).

16. The dental procedure simulator according to any claim 1, wherein said phantom upper jaw comprises an upper support member with a removable upper jaw element removably attached thereto, and wherein said phantom lower jaw comprises a lower support member with a removable lower jaw element removably attached thereto.

17. The dental procedure simulator according to claim 16, wherein said removable upper jaw element is a specific upper jaw element that is provided with phantom teeth.

18. A dental procedure simulator comprising:
a support structure,
a display screen,
a computer configured to simulate a dental procedure or treatment,
a linkage suspended from said support structure, said linkage being controlled by said computer to simulate a medical procedure or treatment by providing haptic force feedback,
a handpiece operably coupled to said linkage and configured to be held in a hand of a user and to be manipulated by the user in a predefined workspace (W) of the dental procedure simulator in real space,
a phantom upper jaw and a phantom lower jaw movably supported by said support structure and arranged in said workspace (W),
said computer being configured to generate an image of the simulated dental procedure for display on a display screen,
wherein said dental procedure simulator comprises a partially transparent reflective element arranged to reflect the image from said display screen to the eyes of the user,
wherein said workspace (W) is arranged to be visible for the user through said partially transparent reflective element, and
wherein said computer is configured to display on said display screen a virtual environment comprising at least one virtual tooth co-located with said phantom upper jaw or with said phantom lower jaw.

19. A dental procedure simulator according to claim 18, configured to reflect said image from said display screen to the eyes of the user by reflection on said partially transparent reflective element and configured to mix said image with a view of said workspace (W) seen by the user through said partially transparent reflective element.

20. A dental procedure simulator according to claim 18, wherein said partially transparent reflective element is a partially transparent mirror or a semi-transparent mirror.

* * * * *